United States Patent [19]

Gebert et al.

[11] Patent Number: 4,833,146
[45] Date of Patent: May 23, 1989

[54] TERTIARY HYDROXYALKYLXANTHINES, MEDICAMENTS CONTAINING THEM AND THEIR USE

[75] Inventors: Ulrich Gebert, Kelkheim; Ismahan Okyayuz-Baklouti, Wiesbaden; Werner Thorwart, Hochheim am Main, all of Fed. Rep. of Germany

[73] Assignee: Hoechst Aktiengesellschaft, Frankfurt am Main, Fed. Rep. of Germany

[21] Appl. No.: 32,729

[22] PCT Filed: Jul. 8, 1986

[86] PCT No.: PCT/EP86/00401
§ 371 Date: Mar. 16, 1987
§ 102(e) Date: Mar. 16, 1987

[87] PCT Pub. No.: WO87/00523
PCT Pub. Date: Jan. 29, 1987

[30] Foreign Application Priority Data

Jul. 19, 1985 [DE] Fed. Rep. of Germany ....... 3525801

[51] Int. Cl.$^4$ ..................... A61K 31/52; C07D 473/04
[52] U.S. Cl. ..................................... 514/263; 544/267
[58] Field of Search ......................... 544/267; 514/263

[56] References Cited

U.S. PATENT DOCUMENTS

| | | |
|---|---|---|
| 2,517,410 | 8/1950 | Papesch ................. 514/267 |
| 4,108,995 | 8/1978 | Mohler et al. ........... 514/267 X |
| 4,575,795 | 5/1985 | Hinze et al. ............ 514/263 |
| 4,576,947 | 3/1986 | Hinze et al. ............ 514/263 |
| 4,713,455 | 12/1987 | Furrer et al. ........... 544/267 |

FOREIGN PATENT DOCUMENTS

| | | |
|---|---|---|
| 1062710 | 9/1979 | Canada . |
| 1075690 | 4/1980 | Canada ................ 544/267 |
| 0017478 | 3/1983 | European Pat. Off. . |
| 1245969 | 8/1967 | Fed. Rep. of Germany . |
| 2432702 | 1/1976 | Fed. Rep. of Germany . |
| 1211333 | 3/1960 | France . |
| 0038284 | 3/1983 | Japan ................. 544/267 |

OTHER PUBLICATIONS

Fieser et al., "Advanced Organic Chemistry", Reinhold Publishing Co., New York, 1961, pp. 270-276.
PCT International Preliminary Examination Report, 6 pages.
Mahler, Schweiz. Med. Wschr., 111 (1981), 637-640.
Raaflaub, Schweiz. Med. Wschr., 110 (1980), 354-362.
Von K. Thiele et al., Arzneim-Forsch/Drug. Res., 34 (I), No. 1 (1984).

Primary Examiner—Donald G. Daus
Assistant Examiner—Diana G. Rivers
Attorney, Agent, or Firm—Finnegan, Henderson, Farabow, Garrett, & Dunner

[57] ABSTRACT

Tertiary hydroxyalkylxanthines having the general formula (I), characterized by the fact that at least one of the residues $R^1$ and $R^3$ represents a tertiary hydroxyalkyl group of formula (Ia) in which $R^4$ represents an alkyl group having up to 3 carbon atoms and n a whole number from 2 to 5; the other residue which may remain $R^1$ or $R^3$ is a hydrogen atom or an aliphatic hydrocarbon residue $R^5$ having up to 6 carbon atoms, in which the carbon chain may be separated by a maximum of two oxygen atoms or be substituted by an oxo group or two hydroxy groups at the most, and $R^2$ represents an alkyl group with 1 to 4 carbon atoms. Also described is a process for manufacturing these compounds, which are suitable for the manufacture of medicines, in particular for use in the prevention and/or treatment of peripheral and/or cerebral irrigation disorders.

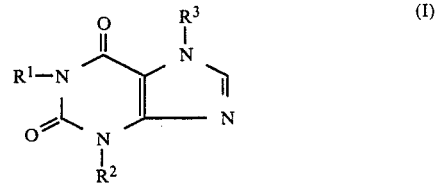

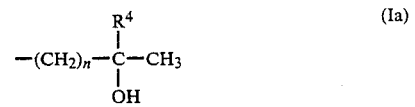

20 Claims, No Drawings

TERTIARY HYDROXYALKYLXANTHINES, MEDICAMENTS CONTAINING THEM AND THEIR USE

The present invention relates to novel xanthine derivatives with at least one tertiary hydroxyalkyl group in the 1- or 7-position, processes for their preparation and their use as active compounds in medicaments which are particularly suitable for the treatment of disturbances in peripheral and cerebral circulation.

1-Oxoalkyl-3,7-dialkyl- and 7-oxoalkyl-1,3-dialkylxanthines and 1-hydroxyalkyl-3,7-dialkyl- and 7-hydroxyalkyl-1,3-dialkylxanthines which have a secondary alcohol group and promote circulation are already known. Within this group of substances, the vasotherapeutic pentoxifylline, 3,7-dimethyl-1-(5-oxohexyl)-xanthine, has acquired considerable therapeutic importance for medicamentous treatment of disturbances both in peripheral and in cerebral circulation. As a vasoactive medicament of the more recent generation (Schweiz. med. Wschr. 111 (1981), pages 637–640), in many countries it now has, for example, a firm place amongst the medicaments used for therapy of peripheral arterial occlusive disease, whilst in some countries it is also used very successfully for deficient cerebral circulation.

The clinically well-established action of this product, however, is counteracted by the disadvantage that both the active compound per se and also its first metabolite, 1-(5-hydroxyhexyl)-3,7-dimethylxanthine, which is also pharmacologically active, are subject to rapid and complete biotransformation in animals and humans, this transformation proceeding almost exclusively via enzymatic oxidation of the oxo- or hydroxyhexyl side chain and being associated with a pronounced "liver first-pass" effect. This means that, especially on oral administration, after absorption from the gastrointestinal tract and transportation via the portal vein system to the liver, the most important filter organ for foreign substances, a considerable proportion of the dose administered is already metabolized by medicament-degrading enzymes in the course of the first passage through the liver, so that in spite of complete absorption, only a certain portion of the drug reaches the systemic, general blood circulation in unchanged form. The "first-pass" effect, also called presystemic elimination, thus leads to a reduction in systemic availability of unchanged active substance. However, the actual handicap of a pronounced "first-pass" effect derives less from the oral dose being reduced en route to the systemic circulation than from the fact that this process as a rule exhibits a wide intra- and interindividual variability (Schweiz. med. Wschr. 110 (1980) pages 354–362), which makes it difficult to draw up definitive dosage plans and thus may impair the therapeutic result.

This unsatisfactory state of affairs is the reason for the understandable desire of clinicians and the intensive search of pharmaceutical researchers for novel xanthine compounds which have a considerably greater metabolic stability, coupled with a similarly good or if possible even more potent pharmacological action and the same outstanding tolerance, and thus have a substantially smaller or even negligible "first-pass" effect and consequently decisively improve the reliability of the therapy in respect of the dosage problems described above. Such products could represent a true advance in medicamentous therapy of disturbances in peripheral and cerebral circulation, which are among the most frequent causes of illness and death in the industrialized countries.

Surprisingly, it has now been found that the hitherto uninvestigated alkyl branching of the secondary hydroxyalkyl radical on the carbon atom carrying the hydroxyl group leads, regardless of whether this radical is in the 1- and/or 7-position on the xanthine skeleton, to compounds in which the hydroxyalkyl side chain, now with a tertiary alcohol structure, is stable towards the polyfunctional microsomal oxidases of the liver and which at the same time also meet the other abovementioned therapeutic requirements.

The present invention thus relates to tertiary hydroxyalkylxanthines of the general formula I (see patent claim 1) in which at least one of the radicals $R^1$ and $R^3$ represents a branched hydroxyalkyl group of the formula

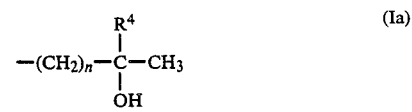

with a tertiary alcohol group in which $R^4$ denotes an alkyl group with 1 to 3 carbon atoms and n denotes an integer from 2 to 5, the other radical which may be present $R^1$ or $R^3$ represents a hydrogen atom or an aliphatic hydrocarbon radical $R^5$ with up to 6 carbon atoms, the carbon chain of which can be interrupted by up to 2 oxygen atoms or substituted by an oxo group or up to two hydroxyl groups, and $R^2$ represents an alkyl group with 1 to 4 carbon atoms.

Preferred compounds here are those of the formula I in which $R^2$ represents a methyl or ethyl group. Those compounds of the formula I in which only one of the two radicals $R^1$ or $R^3$ represents the tertiary hydroxyalkyl group defined above are equally preferred. Those compounds in which $R^4$ represents a methyl group and n denotes an integer from 3 to 5, so that the tertiary hydroxyalkyl radical Ia represents either [(ω-1)-hydroxy-(ω-1)-methyl]-pentyl, -hexyl or -heptyl, and especially those in which $R^2$ denotes methyl or ethyl, are furthermore preferred. Those compounds of the formula I in which $R^1$ represents the tertiary hydroxyalkyl group and $R^3$ represents alkyl, hydroxyalkyl or alkoxyalkyl with in each case 1 to 4 carbon atoms, such as, for example, 7-ethoxymethyl-1-(5-hydroxy-5-methylhexyl)-3-methylxanthine, are moreover to be singled out in particular.

Representative radicals of the group $R^5$ in the position of $R^1$ or $R^3$ are, for example, methyl, ethyl, propyl, isopropyl, butyl, isobutyl, pentyl and hexyl, and the hydroxyl and oxo derivatives thereof, the hydroxyl or oxo group of which is separated from the nitrogen by at least 2 carbon atoms, such as hydroxyethyl, 2- and 3-hydroxypropyl, 2,3-dihydroxypropyl, 2-, 3- and 4-hydroxybutyl, 2-hydroxy-2-methylpropyl, 3,4-dihydroxybutyl, 4,5- and 3,4-dihydroxypentyl, 5,6- and 4,5-dihydroxyhexyl, 4-hydroxypentyl, 5-hydroxyhexyl, 2-oxopropyl, 3-oxobutyl, 4-oxopentyl and 5-oxohexyl, and the alkoxyalkyl and alkoxyalkoxyalkyl groups, such as, for example, methoxy-methyl, -ethyl and -propyl, ethoxy-methyl, -ethyl and -propyl, propoxy-methyl and -ethyl, methoxyethoxy-methyl and -ethyl, and ethoxyethoxy-methyl and -ethyl.

The invention furthermore relates to a process for the preparation of the novel tertiary hydroxyalkylxanthines.

One embodiment comprises, for example, (a) reacting 3-alkylxanthines of the formula II (see patent claim 6) in which $R^2$ represents alkyl with up to 4 carbon atoms with alkylating agents of the formula III (see patent claim 6) in which X represents halogen, preferably chlorine, bromine or iodine, or a sulfonic acid ester or phosphoric acid ester grouping and $R^4$ and n have the abovementioned meanings, to give compounds of the formula Ib according to the invention (see patent claim 6) with a tertiary hydroxyalkyl group in the position of $R^3$ and hydrogen in the position of $R^1$, and (a₁) alkylating these with the same or another alkylating agent of the formula III to give compounds of the formula Ic according to the invention (see patent claim 6) with two identical or different tertiary hydroxyalkyl groups in the positions of $R^1$ and $R^3$, or (a₂) converting these into compounds of the formula Id according to the invention (see patent claim 6) by reaction with a compound of the formula $R^5$—X (IV) in which X has the meaning given in the case of formula III and $R^5$ has the abovementioned meaning, in all cases the reaction advantageously being carried out in the presence of basic agents or the xanthine advantageously being used in the form of their salts.

Another embodiment (b) comprises substituting 1,3-dialkylated xanthines of the formula V (see patent claim 6), advantageously in the presence of basic agents or in the form of their salts, in the 7-position to give compounds of the formula Id by a one-step reaction with a compound of the formula III.

A further embodiment (c) comprises first reacting the 3-alkylxanthines of the formula II, likewise preferably in the presence of basic agents or in the form of their salts, with a compound of the formula $R^6$—X (IVa) to form 3,7-disubstituted xanthines of the formula VI (see patent claim 6) in which $R^6$ has the meaning given for $R^5$ or denotes benzyl or diphenylmethyl, and then substituting these, again preferably in the presence of basic agents or in the form of their salts, in the 1-position with a compound of the formula III, compounds of the formula Ie (see patent claim 6) being obtained, and converting those compounds of the formula Ie in which $R^6$ represents a benzyl or diphenylmethyl group or an alkoxymethyl or alkoxyalkoxymethyl radical into compounds of the formula If according to the invention (see patent claim 6) under reducing or hydrolytic conditions, and, if desired, subsequently reacting the products again with a compound of the formula III or IV to give compounds of the formula Ic or Ie according to the invention.

A further embodiment (d) comprises reducing compounds of the formula Id or Ie according to the invention in which $R^5$ or $R^6$ denotes an oxoalkyl radical, on the keto group with customary reducing agents to give the corresponding hydroxyalkylated xanthines according to the invention.

The 3-alkyl- or 1,3-dialkylxanthines of the formula II or V and "alkylating agents" of the formula III, IV and IVa used here as starting substances are known in most cases, or they can easily be prepared by methods which are known from the literature. Thus, the tertiary alcohols of the formula III can be obtained, for example, by organometallic synthesis by reacting the sterically unhindered halogenoketones of the formula Hal—$(CH_2)_n$—CO—$CH_3$ (VIIa) with alkyl-metal compounds $R^4$—M, in which M denotes a metal, especially magnesium, zinc or lithium, for example in the form of the alkylmagnesium halides $R^4$—MgHal (Grignard compounds) or the alkyllithium compounds $R^4$—Li, in a so-called build-up reaction with reductive alkylation of the carbonyl group under customary conditions (see, for example, Houben-Weyl, volume VI/1a, part 2 (1980), pages 928–40, and in particular pages 1021 et seq. and 1104–1112). A similar reaction for halogenoketones of the formula Hal—$(CH_2)_n$—CO—$R^4$ (VIIb) with methylmagnesium halides or methyllithium likewise leads to the goal.

The hydroxyketones corresponding to the formulae VIIa and VIIb can also be smoothly converted into diols with the alkyl-metal compounds in the customary manner, directly or with temporary masking of the hydroxyl group, for example by acetalization, for example with 5,6-dihydro-4H-pyran (see, for example, Houben-Weyl, volume VI/1a, part 2 (1980), pages 1113–1124), and from these diols compounds of the formula III are formed by selective esterification of the terminal primary hydroxyl group with sulfonic acid halides or anhydrides or phosphoric acid halides or anhydrides, advantageously in the presence of basic agents.

Other possibilities for building up the tertiary alcohol derivatives of the formula III comprise monometallation of ω-chloro-1-bromoalkanes to ω-chloroalkyl-metal compounds (Houben-Weyl, volume XIII/2a (1973), pages 102 and 319) and subsequent reaction thereof with the ketones $R^4$—CO—$CH_3$, the degree of formation of byproducts from the intermediately formed alkanolates due to their tendency to cyclize with elimination of a metal salt being suppressed by appropriate control of the temperature, or the use of ω-halogeno-1-alkanols as starting substances, which are metallated on the hydroxyl group (MO—$(CH_2)_n$—Hal), in the customary manner, preferably in the form of the tetrahydropyran-2-yl ethers or after alkanolate formation carried out with any desired alkyl-metal compound (see, for example, Houben-Weyl, volume XIII/2a, (1973, page 113), the products then being reacted with the ketones $R^4$—CO—$CH_3$ to give the diols mentioned in the preceding paragraph (Houben-Weyl, volume VI/1a, part 2 (1980), page 1029) and the primary hydroxyl group subsequently being selectively esterified with suitable sulfonic acid derivatives or phosphoric acid derivatives.

A convenient access to compounds of the formula III in which $R^4$ represents a methyl group is also offered by the reaction of ω-halogenoalkanoic acid alkyl esters (Hal—$(CH_2)_n$—COO—alkyl) with two equivalents of a methyl-metal compound, the ester reacting via the ketone to give the tertiary alcohol with the introduction of two methyl radicals (Houben Weyl, volume VI/1a, part 2 (1980), pages 1171–1174). ω-Hydroxy-carboxylic acid esters can be converted in the same manner, with or without protection of the hydroxyl group, for example in the form of the tetrahydropyran-2-yl or methoxymethyl ethers or, if appropriate, of the lactones, as cyclic esters, into diols with methyl-metal compounds (see, for example, Houben-Weyl, volume VI/1a, part 2 (1980), pages 1174–1179), from which in turn active alkylating agents of the formula III are obtained by selective esterification of the primary hydroxyl group with sulfonic acid halides or anhydrides or phosphoric acid halides or anhydrides.

Suitable compounds of the formula III which can be prepared by the methods described above are thus the [(ω-1)-hydroxy-(ω-1)-methyl]-butyl, -pentyl, -hexyl and -heptyl, the [(ω-2)-hydroxy-(ω-2)-methyl]-pentyl, -hexyl, -heptyl and -octyl and the [(ω-3)-hydroxy-(ω-3)-methyl]-hexyl, -heptyl, -octyl and -nonyl chlorides, bromides, iodides, sulfonates and phosphates.

Amongst the compounds of the formula $R^5$—X (IV) or $R^6$—X (IVa) which are suitable for introducing $R^5$ into the 1- or 7-position and $R^6$ into the 7-position of the xanthine skeleton, the alkoxymethyl and alkoxyalkoxymethyl derivatives occupy a special place inasmuch as, although halides thereof can be successfully used as reagents, they may present toxicological problems, at least when used on a large industrial scale. In this particular case, the use of the corresponding sulfonates is therefore to be preferred, these being readily accessible, for example, by reaction of mixed anhydrides of aliphatic carboxylic acids and aliphatic or aromatic sulfonic acids (M. H. Karger et al., J. Org. Chem. 36 (1971), pages 528–531) with formaldehyde dialkyl acetals or dialkoxyalkyl acetals in a clear reaction which proceeds virtually to completion (M. H. Karger et al., J. Amer. Chem. Soc. 91 (1969), pages 5663–5665):

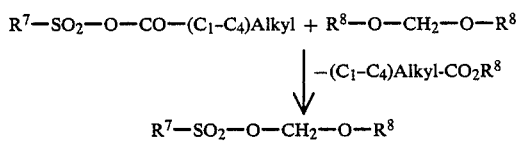

In this equation, $R^7$ represents an aliphatic radical, such as methyl, ethyl or trifluoromethyl, or an aromatic radical, for example phenyl, 4-tolyl or 4-bromophenyl, but preferably methyl or 4-tolyl, and $R^8$ represents an alkyl or alkoxyalkyl group falling within the definition of $R^5$ or $R^6$.

The reaction can be carried out either in bulk or in an anhydrous aprotic solvent which is inert towards the reactants, at temperatures between $-20°$ and $+40°$ C., preferably between 0° and 20° C. Intermediate isolation of the highly reactive sulfonates, which are sensitive towards hydrolysis and unstable to heat, is unnecessary; they are advantageously used directly as crude products for the substitution on the nitrogen of the xanthines, the otherwise customary addition of a basic condensing agent being unnecessary.

The reaction of the mono- or disubstituted xanthine derivatives Ib, If, II, V and VI with the alkylating agents of the formula III or IV or IVa in question is usually carried out in a dispersing agent or solvent which is inert towards the participants in the reaction. Possible dispersing agents or solvents are, in particular, dipolar aprotic solvents, for example formamide, dimethylformamide, dimethylacetamide, N-methylpyrrolidone, tetramethylurea, hexamethylphosphoric acid triamide, dimethyl sulfoxide, acetone and butanone; however, it is also possible to use alcohols, such as methanol, ethylene glycol and mono- or dialkyl ethers thereof, in which the alkyl group has 1 to 4 carbon atoms but both together have not more than 5 carbon atoms, ethanol, propanol, isopropanol and the various butanols; hydrocarbons, such as benzene, toluene or xylenes; halogenated hydrocarbons, such as methylene chloride or chloroform; pyridine and mixtures of the solvents mentioned or mixtures thereof with water.

The "alkylation reactions" are advantageously carried out in the presence of a basic condensing agent. Agents which are suitable for this are, for example, alkali metal or alkaline earth metal hydroxides, carbonates, hydrides and alcoholates, and organic bases such as trialkylamines (for example triethyl- or tributylamine), quaternary ammonium or phosphonium hydroxides and crosslinked resins with fixed, optionally substituted ammonium or phosphonium groups. However, the xanthine derivatives can also be employed in the alkylation reaction directly in the form of their separately prepared salts, for example the alkali metal, alkaline earth metal or optionally substituted ammonium or phosphonium salts. The mono- and disubstituted xanthine compounds can moreover be conveniently alkylated both in the presence of the abovementioned inorganic condensing agents and in the form of their alkali metal or alkaline earth metal salts with the aid of so-called phase transfer catalysts, for example tertiary amines, quaternary ammonium or phosphonium salts or crown ethers, preferably in a two-phase system under the conditions of phase transfer catalysis. Suitable phase transfer catalysts, which are mostly commercially available, are, inter alia, tetra($C_1$-$C_4$)-alkyl- and methyltrioctylammonium and -phosphonium salts, methyl-, myristyl-, phenyl- and benzyltri($C_1$-$C_4$)alkyl- and cetyltrimethylammonium salts and ($C_1$-$C_{12}$)alkyl- and benzyl-triphenylphosphonium salts, as a rule those compounds which have the cation which is larger and of more symmetric structure proving to be more effective.

The introduction of the radicals Ia, $R^5$ and $R^6$ by the procedures described above is in general carried out at a reaction temperature between 0° C. and the boiling point of the particular reaction medium used, preferably between 20° and 130° C., if appropriate under increased or reduced pressure, but usually under atmospheric pressure, it being possible for the reaction time to be from less than one hour to several hours.

The conversion of the 3-alkylxanthines II into the compounds of the formula Ic according to the invention requires the introduction of two tertiary hydroxyalkyl groups. It is possible here either for identical or different substituents to be linked to the xanthine skeleton in succession, or for two identical hydroxyalkyl groups to be linked to the xanthine skeleton in a one-pot reaction, without isolation of intermediate products.

The reductive splitting off of the benzyl and diphenylmethyl groups from compounds of the formula Ie to form the xanthine derivatives If according to the invention which carry a hydrogen atom in the 7-position is carried out under standard conditions which have been developed, in particular, in the context of protective group techniques in alkaloid and peptide syntheses and can thus be assumed to be widely known. As well as chemical reduction, in particular of the benzyl compounds, with sodium in liquid ammonia (Houben-Weyl, volume XI/1 (1957), pages 974–975), elimination of the two abovementioned aralkyl groups by catalytic hydrogenolysis with the aid of a noble metal catalyst is suitable and preferable (Houben-Weyl, volume XI/1 (1957), pages 968–971 and volume IV/1c, part 1 (1980), pages 400–404). The reaction medium used here is usually a lower alcohol (if appropriate with the addition of formic acid or ammonia), an aprotic solvent, such as dimethylformamide or, in particular, glacial acetic acid;

however, mixtures thereof with water can also be used. Suitable hydrogenation catalysts are, in particular, palladium black and palladium-on-active charcoal or barium sulfate, while other noble metals, such as platinum, rhodium and ruthenium frequently give rise to side reactions because of competing nuclear hydrogenation and can therefore be used only to a limited degree. The hydrogenolysis is advantageously carried out at temperatures between 20° and 100° C. under atmospheric pressure or, preferably, a slight increased pressure of up to about 10 bar, as a rule reaction times of a few minutes to several hours being required.

The 1,3,7-trisubstituted xanthines of the formula Ie which carry an alkoxymethyl or alkoxyalkyloxymethyl group in the position of $R^6$ are O,N-acetals. Their substituents in the 7-position can accordingly be split off under the customary conditions of acid hydrolysis (compare Houben-Weyl, volume VI/1b (1984), pages 741–745), the 7H compounds of the formula If likewise being formed. Preferred radicals which can be eliminated by hydrolysis are, for example, the methoxy-, ethoxy- and propoxymethyl and the methoxyethoxy- and ethoxyethoxy-methyl group. The reaction is advantageously carried out with warming in dilute mineral acids, such as hydrochloric or sulfuric acid, if appropriate with an addition of glacial acetic acid, dioxane, tetrahydrofuran or a lower alcohol as the solubilizing agent. Perchloric acid or organic acids, such as trifluoroacetic, formic and acetic acid, together with catalytic amounts of mineral acids are sometimes also suitable. The alkoxyalkoxymethyl compounds in particular can also be split with the aid of Lewis acids, such as zinc bromide and titanium tetrachloride, in an anhydrous medium, preferably in methylene chloride or chloroform, the 7-bromomethyl or 7-bromozinc derivatives intermediately formed hydrolyzing spontaneously in the course of aqueous working up. In the case of splitting in mineral acid solution, the reaction temperature is to be chosen so that no noticeable dehydration of the tertiary hydroxyalkyl group in the 1-position occurs; it should therefore as a rule be less than 100° C.

The reduction of xanthines of the formulae Id and Ie carrying an oxoalkyl group in the position of $R^5$ or $R^6$ to the corresponding hydroxyalkyl compounds can indeed in principle be carried out both with base metals and by catalytic hydrogenation, but the method of choice comprises reaction with simple metal hydrides ($MH_n$), complex metal hydrides ($M^1[M^2H_n]_m$) or organometallic hydrides (Houben-Weyl, volume IV/1d (1981), pages 267–282, and volume VI/1b (1984), pages 141–155), which proceeds under very mild conditions and with high yields. Of the numerous complex metal hydrides which can be used for reduction of ketones, the reagents most frequently used may be mentioned as examples, that is to say lithium alanate, lithium boranate and, in particular, sodium boranate, which is easier to handle because of its lower reactivity and in particular allows the reaction to be carried out in alcoholic, alcoholic-aqueous or purely aqueous solutions or suspensions. Nitriles, such as acetonitrile, can also be used as the reaction medium, as well as the otherwise customary inert solvents, such as ethers (for example diethyl ether, tetrahydrofuran or 1,2-dimethoxyethane), hydrocarbons and pyridine. The hydrogenation, which is advantageously carried out at temperatures between 0° C. and the boiling point of the particular solvent, but preferably at room temperature, as a rule proceeds rapidly and ends within some minutes to a few hours.

The tertiary hydroxyalkylxanthines of the formula I can also be prepared by a procedure in which (e) substituted xanthines of the formula VIII (see patent claim 6), which $e_1$) contain, in the positions of $R^9$ and $R^{10}$, two identical or different groups of the formula $-(CH_2)_n-CO-CH_3$ (IXa) or $-(CH_2)_n-CO-R^4$ (IXb), or only one substituent of the formula IXa or IXb and, in the other position, hydrogen or the radical $R^5$ or $R^6$, are reacted, in the case of the IXa with ($C_1$-$C_3$)alkyl- or in the case of IX with methyl-metal compounds, under reductive "alkylation" of the carbonyl groups to give the xanthines of the formulae Ib to If according to the invention, or ($e_2$) carry, in the positions of $R^9$ and $R^{10}$, two identical or different groups of the formula $-(CH_2)_n-$ Hal (X), in which Hal preferably denotes chlorine or bromine, or only one such radical and hydrogen or the substituent $R^5$ or $R^6$ in the other position, are metallated in the terminal position and then reacted with the ketones of the formula $R^4-CO-CH_3$ (XI) under reductive alkylation of the carbonyl group to give the xanthines of the formulae Ib to If according to the invention, or ($e_3$) carry, in the positions of $R^9$ and/or $R^{10}$, the group $-(CH_2)_n-COO-(C_1-C_4)$alkyl (XII) and, if appropriate, hydrogen or the radical $R^5$ or $R^6$ in the other position, are converted into those xanthines of the formulae Ib to If according to the invention in which $R^4$ denotes methyl by means of two equivalents of a methyl-metal compound per alkoxycarbonyl group, or ($e_4$) carry, in the positions of $R^9$ and $R^{10}$, two identical or different radicals of the formula

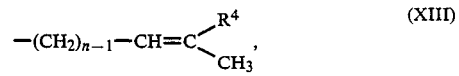

or only one such radical and in the other position hydrogen or the radical $R^5$ or $R^6$, it also being possible for the group XIII to contain the C=C double bond in positionally isomeric locations on the branched carbon atom, for example as

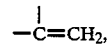

are converted into the xanthines of the formulae Ib to If according to the invention by acid-catalyzed hydration obeying the Markovnikov rule, and, if desired, the tertiary hydroxyalkylxanthines of the formulae Ib and If according to the invention, which carry a hydrogen atom in the 1- or 7-position and are obtained according to methods $e_1$) to $e_4$) are then reacted, if appropriate in the presence of basic agents or in the form of their salts, with the alkylating agents of the formula III or IV or IVa to give the trisubstituted compounds of the formulae Ic or Id or Ie, $R^2$, $R^4$, $R^5$, $R^6$ and n in the above formulae having the abovementioned meanings.

The 3-alkylated mono- or di-oxoalkyl- (VIIIa), -(ω-halogenoalkyl)- (VIIIb), -(ω-alkoxycarbonylalkyl)- (VIIIc) and -alkenyl-xanthines (VIIId) required here as starting substances are either known or can easily be prepared, for example from the 3-alkylxanthines II and the sulfonyloxy- or halogeno-ketones VIIa and VIIb, ω-halogenoalkyl sulfonates or 1,ω-dihalogenoalkanes (compare, for example: V. B. Kalcheva et al., Journal für prakt. Chemie 327 (1985), pages 165-168), ω-sulfonyloxy- or ω-halogeno-carboxylic acid alkyl esters or sulfonyloxy- or halogeno-alkenes of the formula XIII under the reaction conditions which have already been described in detail for the alkylation of mono- and di-substituted xanthines with the compounds of the formulae III and IV.

The procedure followed in the organometallic reactions of the xanthines VIIIa, VIIIb and VIIIc containing functional groups in the radicals $R^9$ and $R^{10}$ is in principle the same as that described for the preparation of the tertiary alcohols of the formula III used as alkylating agents. Thus, the reductive alkylation of the ketones VIIIa and of the esters VIIIc can be carried out, for example, with alkyl-potassium, -sodium, -lithium, -magnesium, -zinc, -cadmium, -aluminum and -tin compounds. The recently recommended alkyl-titanium and -zirconium compounds (D. Seebach et al., Angew. Chem. 95 (1983), pages 12-26) can likewise be employed. However, since the alkyl-metal compounds of sodium and potassium tend to undergo side reactions because of their high reactivity and those of zinc and cadmium are relatively slow to react, the alkyl-lithium and -magnesium (Grignard) compounds are usually preferred.

The highly nucleophilic organometallic compounds are very sensitive towards hydrolysis and oxidation. Their safe handling therefore requires the use of an anhydrous medium, if appropriate under an inert gas atmosphere. The usual solvents or dispersing agents are, in particular, those which are also suitable for the preparation of the alkyl-metal compounds. Possible such solvents or dispersing agents are, in particular, ethers with one or more ether oxygen atoms, for example diethyl, dipropyl, dibutyl or diisoamyl ether, 1,2-dimethoxyethane, tetrahydrofuran, dioxane, tetrahydropyran, furan and anisole, and aliphatic or aromatic hydrocarbons, such as petroleum ether, cyclohexane, benzene, toluene, xylenes, diethylbenzenes and tetrahydronaphthalene; however, it is also possible for tertiary amines, such as triethylamine, or dipolar aprotic solvents, for example hexamethylphosphoric acid triamide, and mixtures of the solvents mentioned to be successfully used. In the reaction of the carbonyl compounds VIIIa and VIIIc with the Grignard compounds of the formula $R^4$-MgHal, a procedure can also advantageously be followed in which the organometallic compound is taken in an ether and the ketone or ester is added dropwise as a solution in methylene chloride or 1,2-dichloroethane. It is frequently advisable to add magnesium bromide, which, because of its participation in the complexlike cyclic transition state is capable of increasing the nucleophilicity of the organometallic compound.

The ketone or ester and organometallic compound are as a rule combined at temperatures between $-20°$ and $100°$ C., preferably between $0°$ and $60°$, or at room temperature without external cooling, the alkyl-metal compound usually being employed in a slight excess. The reaction is then usually brought to completion by heating briefly under reflux, for which time spans from some minutes to a few hours are as a rule sufficient. The decomposition of the alkanolate formed is preferably carried out with aqueous ammonium chloride solution or dilute acetic acid.

Metallic magnesium and lithium, in particular, are suitable for the metallation of the ω-halogenoalkylxanthines VIIIb. In contrast, the replacement of the halogen atom by lithium with the aid of organolithium reagents, usually but-1-yl-, but-2-yl-, tert.-butyl- or phenyl-lithium, which is also possible, plays a minor role. However, the Grignard compounds, which are advantageously prepared in the ethers, hydrocarbons, tertiary amines or aprotic solvents listed as particularly suitable for the reaction of the xanthines VIIIa and VIIIc with alkyl-metal compounds at temperatures between $25°$ and $125°$ C., preferably below $100°$ C., are used in particular. If the metallation reaction is carried out in hydrocarbons, the addition of an ether, such as tetrahydrofuran, or a tertiary amine, such as triethylamine, in a stoichiometric amount frequently proves suitable. The use of catalysts, such as butanol, aluminum chloride, silicon tetrachloride, carbon tetrachloride and aluminum alcoholates or magnesium alcoholates, may also be beneficial. Although the chlorides usually react more slowly than the corresponding bromides and iodides in the halogen/metal replacement, as a rule they give better yields of organometallic compound. The addition of a little magnesium bromide, a few grains of iodine or a few drops of bromine, carbon tetrachloride or methyl iodide, with gentle warming, is frequently recommended to accelerate the onset of the reaction. The Grignard compounds obtained are usually not isolated but reacted directly with the ketones of the formula XI under the reaction conditions described for reductive alkylation of the xanthines VIIIa and VIIIc.

The addition of water onto the C=C double bond of the alkenylxanthines VIIId with the structural element of the formula XIII, in which the hydroxyl group enters on the carbon atom with less hydrogen, in accordance with the Markownikoff rule, to form tertiary alcohols, is usually carried out in aqueous solution or suspension in the presence of strong acids, such as sulfuric, nitric or phosphoric acid. Hydrogen halide acids and sulfonic acids, for example trifluoromethylsulfonic acid, acid exchange resins, boron trifluoride complexes or oxalic acid can also be used as catalysts. However, the reaction is preferably carried out in sulfuric acid, an acid concentration of 50 to 65% and temperatures of $0°$ to $10°$ C. as a rule being sufficient. Lower or higher acid concentrations and/or reaction temperatures can, however, also occasionally be appropriate. The reaction temperature should in all cases be kept as low as possible, since retrograde dehydration to the olefin can manifest itself as an interference reaction at temperatures above about $60°$ C.

The addition of a solvent which is inert towards acids, such as 1,4-dioxane, benzene or toluene, sometimes also provides advantages. Since esters can be intermediately formed during acid-catalyzed hydration, especially when higher acid concentrations are used, it is advisable, after the action of the acid, for the reaction mixture to be treated with a large amount of water, with brief warming, or to be worked up under alkaline conditions, for the purpose of ester hydrolysis.

The experimental conditions for the optional conversion of the 1- and 7H compounds Ib and If according to the invention into the trisubstituted xanthines of the formulae Ic or Id or Ie by N-alkylation with the compounds III or IV or IVa have already been described in detail.

In the compounds in which one of the radicals $R^1$ and $R^3$ represents a dihydroxyalkyl group, this dihydroxyalkyl group can be built up or introduced by customary methods, such as are described, for example, in European Offenlegungsschrift No. 75,850.

The tertiary hydroxyalkylxanthines of the formula I can have one or two asymmetric carbon atoms, depending on the chain length of the alkyl radical $R^4$ (at least $C_2$) and/or the structure of the substituent $R^5$ (for example 2-hydroxypropyl), and can thus exist in steroisomeric (sic) forms. The invention therefore relates both to the pure stereoisomeric compounds and to mixtures thereof.

Because of their useful pharmacological and favorable metabolic properties, for example in respect of the polyfunctional microsomal oxidases of the liver, the xanthine compounds of the formula I according to the invention are outstandingly suitable for use as active compounds in medicaments, in particular in those which make possible a more effective prophylactic and curative treatment of diseases caused by disturbances in peripheral and cerebral circulation, such as peripheral arterial occlusive disease, and thus represent a substantial enrichment of the range of medicaments available. They can be administered either by themselves, for example in the form of microcapsules, in mixtures with one another or in combination with suitable excipients.

The invention consequently also relates to medicaments containing at least one compound of the formula I as the active compound.

The medicaments according to the invention are in general administered orally or parenterally, but rectal use is in principle also possible. Examples of suitable solid or liquid pharmaceutical formulations are granules, powders, tablets, coated tablets, (micro)capsules, suppositories, syrups, emulsions, suspensions, aerosols, drops or injectable solutions in ampule form and products with a protracted release of active compound, for the preparation of which auxiliaries, such as excipients, disintegrating agents, binders, coating agents, swelling agents, lubricants or greasing agents, flavoring agents, sweeteners or solubilizing agents, are usually used. Frequently used auxiliaries which may be mentioned are, for example, magnesium carbonate, titanium dioxide, lactose, mannitol and other sugars, talc, milk protein, gelatin, starch, vitamins, cellulose and their derivatives, animal and vegetable oils, polyethylene glycols and solvents, such as, for example, sterile water, alcohols, glycerol and polyhydric alcohols.

The pharmaceutical products are preferably prepared and administered in dosage units, each unit containing a particular dose of a compound of the formula I as the active constituent. In solid dosage units, such as tablets, capsules and suppositories, this dose can be up to 1000 mg, but preferably 100 to 600 mg, and in injection solutions in ampule form it can be up to 300 mg, but preferably 20 to 200 mg.

Daily doses of 100 to 2000 mg of active compound, preferably 300 to 900 mg, for oral administration, and of 10 to 500 mg, preferably 20 to 200 mg, for intravenous administration, are indicated for the treatment of an adult patient—depending on the activity of the compounds of the formula I on humans. In certain circumstances, however, higher or lower daily doses may also be appropriate. The daily dose can be administered either by a single dose in the form of an individual dosage unit or several smaller dosage units or by multiple administration of subdivided doses at certain intervals.

Finally, the xanthine derivatives of the formula I can also be formulated, in the preparation of the abovementioned pharmaceutical formulations, together with other suitable active compounds, for example antithrombotics, antihyperlipidemics, analgesics, sedatives, antidepressants, antianginal agents, cardiotonics, antiarrhythmics, diuretics, antihypertensives, including $\beta$-receptor blockers and calcium channel blockers, plasma expanders and other vasotherapeutics.

The structure of all the compounds described below has been confirmed by elemental analysis and IR and $^1$H-NMR spectra. The compounds of the formula I prepared in accordance with the following examples 1 to 14 and 55 and 56 and compounds 15 to 54 of the formula I, which are prepared in an analogous manner, are summarized in Table 1. Ether below is in each case understood as diethyl ether, and a vacuum is understood as that of a water pump.

EXAMPLE 1

7-(5-Hydroxy-5-methylhexyl)-3-methylxanthine (a)

1-Chloro-5-hydroxy-5-methylhexane

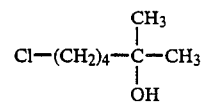

(a₁) from 1-chloro-5-hexanone: A solution of 67.3 g (0.5 mol) of 1-chloro-5-hexanone in 50 ml of anhydrous ether is added dropwise to 44.9 g (0.6 mol) of methylmagnesium chloride in the form of a 20% strength solution in tetrahydrofuran and 200 ml of dry ether at 0° to 5° C., while stirring. The mixture is then subsequently stirred initially at room temperature for one hour and then while boiling under reflux for a further hour, the tertiary alkanolate formed is decomposed by addition of 50% strength aqueous ammonium chloride solution, the ether phase is separated off and the aqueous phase is extracted by shaking with ether. The combined ethereal extracts are washed in succession with aqueous sodium bisulfite solution and sodium bicarbonate solution as well as a little water, dried over sodium sulfate, filtered and concentrated in vacuo and the liquid residue is subjected to fractional distillation under reduced pressure.

Yield: 64.1 g (85.1% of theory), boiling point (20 mbar) 95°–97° C., refractive index $n_D^{25}=1.4489$, $C_7H_{15}ClO$ (molecular weight=150.65).

It was also possible to prepare the compound in an analogous manner from methyl or ethyl 5-chloropentanoate with twice the molar amount of methylmagnesium chloride (compare Example 13a).

(a₂) From 1-bromo-4-chlorobutane and acetone: 24.3 g (1 gram atom) of magnesium are covered with a layer of anhydrous ether and 10 g of 1-bromo-4-chlorobutane are added. As soon as the reaction has started up, a further 161.5 g of dihalogenoalkane (a total of 1 mol), dissolved in 200 ml of dry ether, are added dropwise so that the reaction mixture boils gently.

When the reaction of the metal has ended, 52.3 g (0.9 mol) of acetone are added dropwise and the mixture is mixed with the same volume of dry ether. After subsequently stirring at room temperature for 2 hours, 100 g of ice and saturated ammonium chloride solution are added, the ethereal layer is separated off and the aqueous phase is extracted several times with ether. The combined organic phases are washed with a little water and dried over sodium sulfate, the ether is distilled off in vacuo and the liquid residue is fractionated under reduced pressure.

Yield: 71.6 g (52.8% of theory), boiling point (17 mbar) 95° C.

(b)

7-(5-Hydroxy-5-methylhexyl)-3-methylxanthine

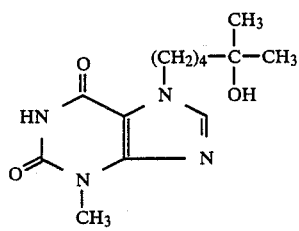

83 g (0.5 mol) of 3-methylxanthine are dissolved in 500 ml of 1N sodium hydroxide solution (0.5 mol) under the influence of heat. The mixture is filtered, the water is distilled off under reduced pressure and the sodium salt which remains is dried under a high vacuum. After addition of 1.5 liters of dimethylformamide and 75.3 g (0.5 mol) of 1-chloro-5-hydroxy-5-methylhexane, the mixture is heated at 110° C. for 6 hours, while stirring, filtered hot and evaporated under reduced pressure, the residue obtained is taken up in 1 liter of hot 1N sodium hydroxide solution, the hot solution is filtered and, after cooling to room temperature, 6N hydrochloric acid is added dropwise, with stirring, until a pH of 9 is reached. The precipitate is filtered off with suction, washed neutral and dried in vacuo.

Yield: 100.5 g (71.7% of theory), melting point: 228°–230° C., $C_{13}H_{20}N_4O_3$ (molecular weight=280.3).

Analysis: Calculated: C 55.70% H 7.19% N 19.99%. Found: C 55.60% H 7.31% N 19.92%.

EXAMPLE 2

1,7-Bis-(5-hydroxy-5-methylhexyl)-3-methylxanthine

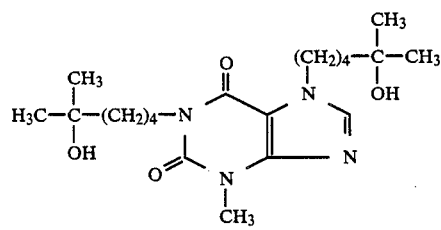

A mixture of 14 g (0.05 mol) of 7-(5-hydroxy-5-methylhexyl)-3-methylxanthine (Example 1b), 8.2 g (0.054 mol) of 1-chloro-5-hydroxy-5-methylhexane (Example 1a) and 7.5 g (0.054 mol) of potassium carbonate in 300 ml of dimethylformamide is stirred at 110° C. for 18 hours and then filtered hot and the filtrate is concentrated under reduced pressure. The residue is taken up in chloroform, the mixture is washed first with dilute sodium hydroxide solution and then with water until neutral and dried over sodium sulfate and the solvent is distilled off in vacuo. The crude product can advantageously be obtained in the analytically pure form by filtration over a silica gel column in the solvent mixture chloroform/methanol (10:1) and subsequent extraction by stirring in diisopropyl ether.

Yield: 14.9 g (75.5% of theory), melting point: 93°–95° C., $C_{20}H_{34}N_4O_4$ (molecular weight=394.5).

Analysis: Calculated: C 60.89% H 8.69% N 14.20%. Found: C 60.89% H 8.98% N 14.17%.

The same compound was also obtained, inter alia, by a one-stage dialkylation of 3-methylxanthine with twice the molar amount of 1-chloro-5-hydroxy-5-methylhexane or by reaction of 1,7-bis-(5-oxohexyl)-3-methylxanthine with two equivalents of methylmagnesium chloride or bromide in anhydrous tetrahydrofuran.

EXAMPLE 3

7-(5-Hydroxy-5-methylhexyl)-3-methyl-1-propylxanthine

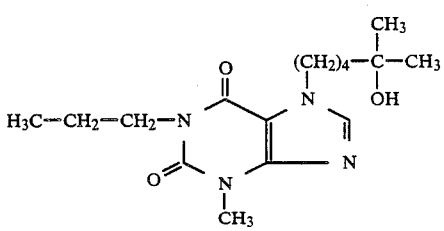

40 g (0.14 mol) of 7-(5-hydroxy-5-methylhexyl)-3-methylxanthine (Example 1b) are heated at 130° C. together with 18.5 g (0.15 mol) of 1-bromopropane and 20.7 g (0.15 mol) of potassium carbonate in 300 ml of dimethylformamide for 8 hours, while stirring. After cooling and concentrating under reduced pressure, dilute sodium hydroxide solution is added to the residue and the mixture is extracted thoroughly with chloroform. After the organic phase has been washed neutral with water, dried over sodium sulfate and evaporated under reduced pressure, an oily crude product is obtained which, for simplicity, is purified by filtration over a silica gel column in the solvent mixture chloroform/methanol (25:1) and extraction by stirring in diisopropyl ether.

Yield: 36.5 g (80.9% of theory), melting point: 59°–60° C., $C_{16}H_{26}N_4O_3$ (molecular weight=322.4).

Analysis: Calculated: C 59.61% H 8.13% N 17.38%. Found: C 59.43% H 8.01% N 17.29%.

Both alkylation of 3-methyl-1-propylxanthine with 1-chloro-5-hydroxy-5-methylhexane analogously to the following example 4 and Grignard synthesis with 3-methyl-7-(5-oxohexyl)-1-propylxanthine and methylmagnesium bromide or chloride in anhydrous tetrahydrofuran led to the same compound.

EXAMPLE 4

7-(5-Hydroxy-5-methylhexyl)-1,3-dimethylxanthine

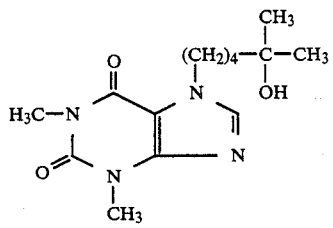

21.8 g (0.1 mol) of 1,3-dimethylxanthine in the form of the potassium salt (prepared analogously to Example 1b from 1,3-dimethylxanthine and an equimolar amount of potassium hydroxide in water) are stirred with 16.6 g (0.11 mol) of 1-chloro-5-hydroxy-5-methylhexane of Example 1a in 50 ml of dimethylformamide at 120° C.

for 18 hours. The mixture is allowed to cool and is concentrated in vacuo, 4N sodium hydroxide solution is added and the product is extracted with chloroform. The extract is washed neutral with water, dried and evaporated under reduced pressure and the residue is recrystallized from isopropanol/ether.

Yield: 20.7 g (70.3% of theory), melting point: 106°–107° C., $C_{14}H_{22}N_4O_3$ (molecular weight=294.36).

Analysis: Calculated: C 57.13% H 7.53% N 19.03%. Found: C 57.39% H 7.67% N 19.28%.

Alternatively, it was possible to prepare the compound, inter alia, from 7-(5-hydroxy-5-methylhexyl)-3-methylxanthine (Example 1b) and iodomethane analogously to Example 3, from 1,3-dimethyl-7-(5-oxohexyl)-xanthine and methylmagnesium chloride or bromide in anhydrous ether analogously to Example 9, and from 1,3-dimethyl-7-(5-methyl-4-hexenyl)-xanthine by acid-catalyzed hydration analogously to Example 14.

EXAMPLE 5

7-Ethoxymethyl-1-(5-hydroxy-5-methylhexyl)-3-methylxanthine (a)

7-Ethoxymethyl-3-methylxanthine

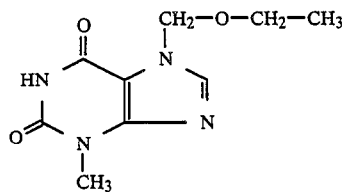

(a₁) with ethoxymethyl chloride: 83 g (0.5 mol) of 3-methylxanthine are dissolved in a solution of 20 g (0.5 mol) of sodium hydroxide in 400 ml of water under the influence of heat. After filtration, the filtrate is concentrated in vacuo, methanol is distilled over several times and the sodium salt is dried under a high vacuum.

The dry salt is suspended in 1.3 liters of dimethylformamide, 47.3 g (0.5 mol) of ethoxymethyl chloride are added while stirring, and the mixture is stirred at 110° C. for 18 hours. It is then filtered hot, the filtrate is evaporated in vacuo, the residue is dissolved in 500 ml of 2N sodium hydroxide solution and the solution is extracted by shaking with chloroform in order to remove the 1,7-dialkylated 3-methylxanthine formed as a byproduct. The aqueous alkaline solution is brought to pH 9 with 2N hydrochloric acid, while stirring, and the crystals formed are filtered off with suction, washed first with water until free from chloride and then with methanol and dried in vacuo.

Yield: 77.6 g (69.2% of theory), melting point: 263°–264° C., $C_9H_{12}N_4O_3$ (molecular weight=224.2).

(a₂) with ethoxymethyl 4-toluenesulfonate (starting from 4-toluenesulfonyl chloride and sodium acetate): 104.9 (0.55 mol) of 4-toluenesulfonyl chloride are dissolved in 100 ml of dimethylformamide, and 45.1 g (0.55 mol) of anhydrous sodium acetate are introduced, while stirring and cooling with ice. After the mixture has been subsequently stirred at room temperature for one hour, 78.1 g (0.75 mol) of formaldehyde diethylacetal are added dropwise. The mixture is again stirred at room temperature for one hour and 83 g (0.5 mol) of 3-methylxanthine are then added. Thereafter, the reaction mixture is heated at 90° C. for two hours, without the addition of a basic condensing agent, and is cooled and the product precipitated is filtered off cold with suction, rinsed with a little cold dimethylformamide, washed with water until free from chloride, rinsed with methanol and recrystallized from dimethylformamide.

Yield: 98.1 g (87.5% of theory), melting point: 265° C.

(a₃) with ethoxymethyl 4-toluenesulfonate (starting from 4-toluenesulfonic acid and acetic anhydride): 226 g (1.2 mol) of 4-toluenesulfonic acid monohydrate are dissolved in 450 g (4.4 mol) of acetic anhydride, while stirring and coolng, and the solution is then warmed at 70° C. for 30 minutes. The acetic acid formed and excess acetic anhydride are distilled off under reduced pressure, the residue is diluted with 100 ml of toluene and the resulting solutions is stirred into 450 ml of dimethylformamide, while cooling, so that the internal temperature does not rise above 20° C. After dropwise addition of 230 g (2.2 mol) of formaldehyde diethyl acetal and subsequent stirring at 20° C. for one hour, 166.1 g (1 mol) of 3-methylxanthine are added. The reaction mixture is warmed, stirred at 100° C. for one hour and then cooled and the product which has precipitated is filtered off with suction, washed in succession with in each case 250 ml of dimethylformamide, water and methanol and recrystallized from dimethylformamide.

Yield: 201 g (89.7% of theory), melting point: 264°–265° C.

(b)

7-Ethoxymethyl-1-(5-hydroxy-5-methylhexyl)-3-methylxanthine

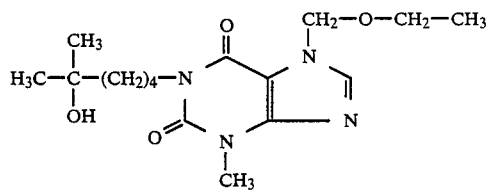

7.5 g (0.054 mol) of potassium carbonate and 8.2 g (0.054 mol) of 1-chloro-5-hydroxy-5-methylhexane (Example 1a) are added to 11.2 g (0.05 mol) of 7-ethoxymethyl-3-methylxanthine in 300 ml of dimethylformamide and the mixture is heated at 110° C. for 5 hours, while stirring. The mixture is filtered hot with suction, the filtrate is concentrated in vacuo, the residue is taken up in chloroform, the mixture is washed first with 1N sodium hydroxide solution and then with water until neutral and dried over sodium sulfate, the solvent is distilled off under reduced pressure and the residue is recrystallized from diisopropyl ether, and the addition of ethyl acetate and petroleum ether.

Yield: 14.1 g (83.3% of theory), melting point: 102°–103° C., $C_{16}H_{26}N_4O_4$ (molecular weight=338.4).

Analysis: Calculated: C 56.79% H 7.74% N 16.56%. Found: C 56.76% H 7.82% N 16.59%.

The compound was also obtained, for example, by Grignard synthesis from 7-ethoxymethyl-3-methyl-1-(5-oxohexyl)xanthine with methylmagnesium chloride in anhydrous ether analogously to Example 9.

EXAMPLE 6

1-(5-Hydroxy-5-methylhexyl)-3-methylxanthine (a)

by catalytic hydrogenolysis from 7-benzyl-1-(5-hydroxy-5-methylhexyl)-3-methylxanthine 7-Benzyl-3-methylxanthine

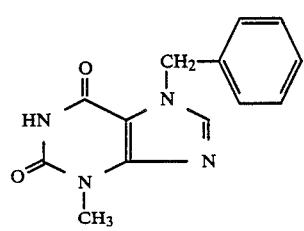

20 g (0.5 mol) of sodium hydroxide dissolved in 200 ml of water are added to a suspension of 83 g (0.5 mol) of 3-methylxanthine in 500 ml of methanol, the mixture is stirred at 70° C. for one hour, 85.5 g (0.5 mol) of benzyl bromide are then added dropwise at the same temperature and the reaction mixture is kept between 70° and 80° C. for 5 hours. It is then cooled and filtered cold with suction, the product on the suction filter is washed with water and dissolved in 1000 ml of 1N sodium hydroxide solution under the influence of heat, the solution is filtered and the pH is brought slowly to 9.5 with 4N hydrochloric acid, while stirring. The crystals are filtered off from the still warm solution, washed with water until free from chloride and dried in vacuo.

Yield: 81.7 g (63.8% of theory), melting point: 262°–264° C.), $C_{13}H_{12}N_4O_2$ (molecular weight=256.2).

7-Benzyl-1-(5-hydroxy-5-methylhexyl)-3-methylxanthine

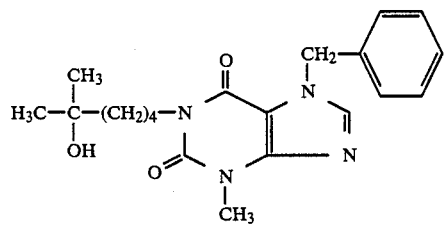

A mixture of 20.5 g (0.08 mol) of 7-benzyl-3-methylxanthine, 12.4 g (0.09 mol) of potassium carbonate and 13.6 l g (0.09 mol) of the tertiary alcohol from Example 1a in 300 ml of dimethylformamide is heated at 110° to 120° C. for 8 hours, while stirring, and is then filtered hot and the filtrate is evaporated under reduced pressure. The residue is taken up in chloroform, the mixture is washed first with 1N sodium hydroxide solution and then with water until neutral and dried, the solvent is distilled off in vacuo and the solid residue is recrystallized from ethyl acetate, with the addition of petroleum ether.

Yield: 23.8 g (80.3% of theory), melting point: 109°–111° C., $C_{20}H_{26}N_4O_3$ (molecular weight=370.5).

Analysis: Calculated: C 64.84% H 7.07% N 15.12%. Found: C 65.00% H 7.21% N 15.24%.

The compound was also accessible, inter alia, by first reacting 7-benzyl-3-methylxanthine with 1-chloro-5-hexanone under the reaction conditions described above to give 7-benzyl-3-methyl-1-(5-oxohexyl)-xanthine (yield 90.4% of theory, melting point: 82°–84° C.) and then reductively methylating the oxohexyl side chain with methylmagnesium chloride in anhydrous ether analogously to Example 9 (yield: 60.2% of theory; melting point: 108°–110° C.).

1-(5-Hydroxy-5-methylhexyl)-3-methylxanthine

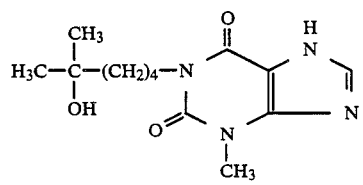

14.8 g (0.04 mol) of the abovementioned 7-benzylxanthine are hydrogenated in 200 ml of glacial acetic acid over 1.5 g of palladium (5%) on active charcoal at 60° C. under 3.5 bar in the course of 24 hours, while shaking. After cooling, the mixture is blanketed with nitrogen, the catalyst is filtered off, the filtrate is concentrated under reduced pressure and the solid residue is recrystallized from ethyl acetate.

Yield: 9.6 g (85.6% of theory), melting point: 192°–193° C., $C_{13}H_{20}N_4O_3$ (molecular weight=280.3).

Analysis: Calculated: C 55.70% H 7.19% N 19.99%. Found: C 55.63% H 7.30% N 20.00%.

(b)

by hydrolytic dealkoxymethylation from 7-ethoxymethyl-1-(5-hydroxy-5-methylhexyl)-3-methylxanthine of Example 5b 13.5 g (0.04 mol) of the xanthine compound of Example 5b are heated at 70° C. in a mixture of 300 ml of 1N hydrochloric acid and 30 ml of glacial acetic acid for 2.5 hours, while stirring, and, after cooling, the mixture is neutralized with 4N sodium hydroxide solution and the product is extracted with chloroform. The chloroform extract is dried and evaporated to dryness in vacuo and, after filtration over a silica gel column in the mobile phase chloroform/methanol (10:1), the residue is recrystallized from ethyl acetate.

Yield: 7.7 g (68.7% of theory), melting point: 191°–192° C.

Similar hydrolytic splitting off of the propoxymethyl radical from 1-(5-hydroxy-5-methylhexyl)-3-methyl-7-propoxymethylxanthine (Example 34) gave the 7H-compound in 75% yield.

EXAMPLE 7

1-(5-Hydroxy-5-methylhexyl)-3-methyl-7-(2-oxopropyl)-xanthine (a)

3-Methyl-7-(2-oxopropyl)-xanthine

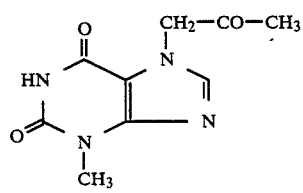

166 g (1 mol) of 3-methylxanthine and 110 g (1.3 mol) of sodium bicarbonate are suspended in 500 ml of dimethylformamide, the suspension is heated to 100° C., while stirring, and 111 g (1.2 mol) of chloroacetone are added dropwise over a period of 2 hours. The mixture is then subsequently stirred at 100° C. for two hours and thereafter cooled and the precipitate formed is filtered off with suction and washed five times with 50 ml of dimethylformamide each time. After the product has been taken up in warm 1N sodium hydroxide solution at 60° C., dilute hydrochloric acid is added until the pH reaches 9, the mixture is filtered hot with suction and the residue is washed with water until free from chloride, rinsed with methanol and dried at 80° C. in a drying cabinet.

Yield: 190 g (85.5% of theory), melting point: 300° C., $C_9H_{10}N_4O_3$ (molecular weight = 222.2).

When sodium carbonate or potassium carbonate was used as the basic condensing agent or the sodium salt or potassium salt of 3-methylxanthine was employed, the yields were considerably lower (not more than 70%).

(b)

1-(5-Hydroxy-5-methylhexyl)-3-methyl-7-(2-oxopropyl)-xanthine

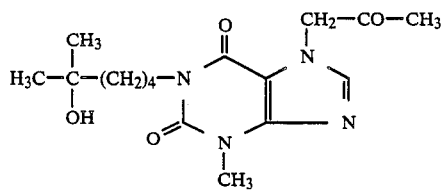

22.2 g (0.1 mol) of the xanthine from stage (a) are reacted with 16.6 g (0.11 mol) of 1-chloro-5-hydroxy-5-methylhexane (Example 1a) and 15.2 g (0.11 mol) of potassium carbonate in 500 ml of dimethylformamide and the mixture is worked up, under the experimental conditions described in Example 2. The reaction product is purified by column chromatography and finally recrystallized from diisopropyl ether, with the addition of ethyl acetate, at the boiling point.

Yield: 26.7 g (79.4% of theory), melting point: 78°–80° C., $C_{16}H_{24}N_4O_4$ (molecular weight = 336.4).

Analysis: Calculated: C 57.13% H 7.19% N 16.66%. Found: C 56.85% H 7.28% N 16.41%.

EXAMPLE 8

1-(5-Hydroxy-5-methylhexyl)-7-(2-hydroxypropyl)-3-methylxanthine

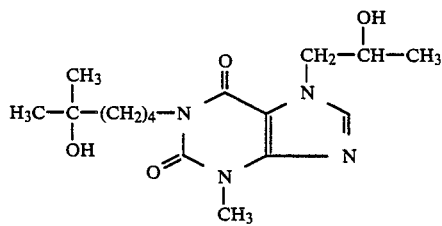

0.95 g (0.025 mol) of sodium boranate is added to a suspension of 16.8 g (0.05 mol) of 1-(5-hydroxy-5-methylhexyl)-3-methyl-7-(2-oxopropyl)-xanthine (Example 7b) in 200 ml of methanol at room temperature, while stirring. After the mixture has been stirred for one hour, a clear solution has formed. The excess hydride is decomposed by addition of 1 ml of glacial acetic acid, the mixture is evaporated under reduced pressure, the residue is taken up in chloroform and the mixture is washed in succession with dilute sodium hydroxide solution and water, dried over sodium sulfate and concentrated to dryness in vacuo. The solid crude product is recrystallized from ethyl acetate.

Yield: 15.3 g (90.4% of theory), melting point: 119°–120° C., $C_{16}H_{26}N_4O_4$ (molecular weight = 338.4).

Analysis: Calculated: C 56.79% H 7.74% N 16.56%. Found: C 56.52% H 7.86% N 16.47%.

It was also possible to build up the compound starting from 3-methylxanthine in a two-stage reaction sequence, by first introducing the 2-hydroxypropyl group into the 7-position (melting point: 278°–280° C.; yield: 69.6% of theory) with 1-chloro-2-propanol and then alkylating the product in the 1-position (yield: 67.5% of theory) with 1-chloro-5-hydroxy-5-methylhexane (Example 1a).

EXAMPLE 9

1-(5-Hydroxy-5-methylhexyl)-3-methyl-7-propylxanthine

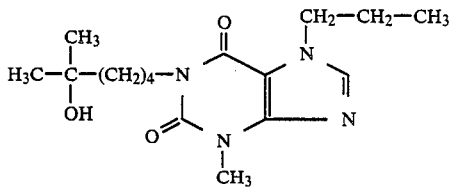

22.4 g (0.3 mol) of methylmagnesium chloride is added dropwise in the form of a 20% strength solution in tetrahydrofuran to a suspension of 61.3 g (0.2 mol) of 3-methyl-1-(5-oxohexyl)-7-propylxanthine in 2 liters of anhydrous ether at room temperature, while stirring vigorously, the internal temperature rising to about 30° C. The mixture is then heated under reflux for 2 hours, while stirring, saturated aqueous ammonium chloride solution is added to dissociate the alkanolate formed and the organic phase is separated off and washed twice with 500 ml of water each time. The aqueous phases are collected and extracted again thoroughly with methylene chloride. The methylene chloride extract is combined with the ethereal phase and the mixture is dried over sodium sulfate, filtered and evaporated under reduced pressure, whereupon 59.0 g of crude product (91.5% of theory) are obtained and are purified by recrystallization from diisopropyl ether.

Yield: 49.8 g (77.2% of theory), melting point: 81°–82° C., $C_{16}H_{26}N_4O_3$ (molecular weight = 322.4).

Analysis: Calculated: C 59.61% H 8.13% N 17.38%. Found: C 59.72% H 8.09% N 17.44%.

The course of the reaction is more favorable if the Grignard solution is taken and diluted with 200 ml of anhydrous ether, the 3-methyl-1-(5-oxohexyl)-7-propylxanthine, dissolved in 300 ml of dry methylene chloride, is added dropwise at 10° to 15° C., while stirring, and the mixture is subsequently stirred at room temperature for one hour, during which the ketone reacts completely. The aqueous ammonium chloride solution is added, the organic solvents are distilled off under reduced pressure and the tertiary alcohol is extracted with chloroform. The yield of pure product is 92.1% of theory.

The same compound was obtained, inter alia, by alkylation of the compound of Example 6 with 1-bromo- or 1-chloropropane analogously to Example 3, by reaction of 3-methyl-7-propylxanthine with the tertiary alcohol of Example 1a analogously to Example 2, or by acid-catalyzed hydration of 3-methyl-1-(5-methyl-4-hexenyl)-7-propylxanthine analogously to Example 14 below.

EXAMPLE 10

1-(5-Hydroxy-5-methylheptyl)-3,7-dimethylxantine

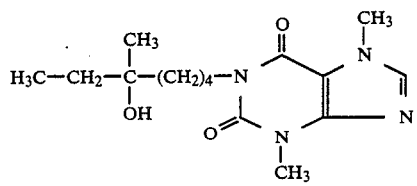

20.0 g (0.15 mol) of ethylmagnesium bromide are taken as a 40% strength solution in ether, and 27.8 g (0.1 mol) of 3,7-dimethyl-1-(5-oxohexyl)-xanthine in 1 liter of dry ether are metered in dropwise at room temperature, while stirring, whereupon a voluminous precipitate forms. The mixture is heated and is subsequently stirred, while boiling gently under reflux, for one hour. It is then worked up as described in the preceding Example 9 to give 25 g of oily crude product (81.1% of theory), which gradually crystallizes completely and is purified by recrystallization from diisopropyl ether, with the addition of a little ethyl acetate, at the boiling point.

Yield: 22.9 g (74.3% of theory), melting point: 83°–84° C., $C_{15}H_{24}N_4O_3$ (molecular weight=308.4).

Analysis: Calculated: C 58.42% H 7.84% N 18.17%. Found: C 58.33% H 8.02% N 18.21%.

EXAMPLE 11

1-(5-Hydroxy-5-methylhexyl)-7-(2-hydroxy-2-methylpropyl)-3-methylxanthine (a)

3-Methyl-1-(5-oxohexyl)-7-(2-oxopropyl)-xanthine

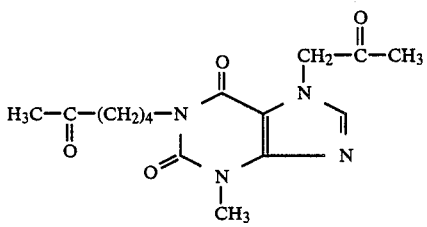

22.2 g (0.1 mol) of 3-methyl-7-(2-oxopropyl)-xanthine from Example 7a are stirred together with 14.8 g (0.11 mol) of 1-chloro-5-hexanone and 15.2 g (0.11 mol) of potassium carbonate in 500 ml of dimethylformamide at 110° C. for 1.5 hours. The mixture is then allowed to cool slowly, with further stirring, and filtered, the salt on the suction filter is rinsed thoroughly with dimethylformamide, the solution is concentrated under reduced pressure, the residue is taken up in 200 ml of methanol, 50 ml of water and 2 ml of concentrated sulfuric acid are added and the mixture is boiled under reflux for one hour. After removal of the methanol in vacuo, the residue is rendered alkaline with 33% strength sodium hydroxide solution and the mixture is extracted thoroughly by shaking with chloroform. The combined chloroform extracts are washed with a little water until neutral and dried over sodium sulfate and the solvent is distilled off in vacuo, whereupon 25.8 g of solid crude product (80.5% of theory) are obtained and are recrystallized from ethanol, with the addition of petroleum ether, at the boiling point.

Yield: 23.1 g (72.1% of theory), melting point: 111°–113° C., $C_{15}H_{20}N_4O_4$ (molecular weight=320.3).

Analysis: Calculated: C 56.24% H 6.29% N 17.49%. Found: C 56.31% H 6.35% N 17.21%.

(b)

1-(5-Hydroxy-5-methylhexyl)-7-(2-hydroxy-2-methylpropyl)-3-methylxanthine

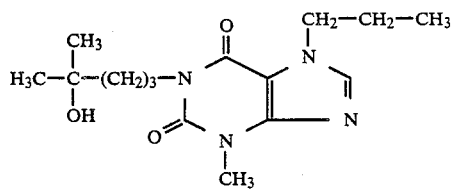

32.0 g (0.1 mol) of the di-oxoalkylated xanthine from stage (a) in 100 ml of anhydrous methylene chloride are slowly added to 22.4 g (0.3 mol) of methylmagnesium chloride in the form of the commercially available 20% strength solution in tetrahydrofuran at room temperature, with exclusion of moisture and vigorous stirring. When the addition has ended, the reaction mixture is heated and is kept at the reflux temperature for 2 hours, before it is worked up in accordance with Example 9 and the crude product is recrystallized from ethyl acetate.

Yield: 25.8 g (73.2% of theory), melting point: 121°–123° C., $C_{17}H_{28}N_4O_4$ (molecular weight=352.4).

Analysis: Calculated: C 57.93% H 8.01% N 15.90%. Found: C 57.70% H 7.93% N 15.83%.

The compound was also obtained, inter alia, by a two-stage synthesis from 3-methylxanthine, which was first reacted with 1-chloro-2-hydroxy-2-methylpropane to give 7-(2-hydroxy-2-methylpropyl)-3-methylxanthine (melting point: 268°–269° C.; yield 51% of theory), the product then being alkylated in the 1-position with 1-chloro-5-hydroxy-5-methylhexane from Example 1a analogously to Example 5b to give the end product (yield: 79.5% of theory).

EXAMPLE 12

1-(4-Hydroxy-4-methylpentyl)-3-methyl-7-propylxanthine (a)

1-Chloro-4-hydroxy-4-methylpentane 44.9 g (0.6 mol) of methylmagnesium chloride, as a 20% strength solution in tetrahydrofuran, are reacted in anhydrous ether with 60.3 g (0.5 mol) of 1-chloro-4-pentanone, and the mixture is worked up, according to Example 1a₁

Yield: 42.7 g (62.5% of theory), boiling point (17 mbar) 77°–78° C., $C_6H_{13}ClO$ (molecular weight=136.6).

(b)

1-(4-Hydroxy-4-methylpentyl)-3-methyl-7-propylxan-
thine

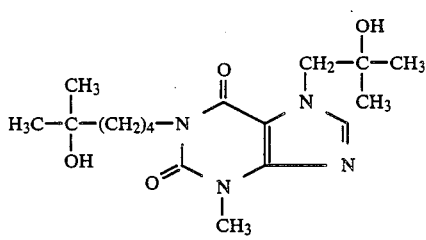

A solution of 5.6 g (0.1 mol) of potassium hydroxide in 100 ml of methanol is added to a suspension of 20.8 g (0.1 mol) of 3-methyl-7-propylxanthine in 250 ml of methanol. On heating, a clear solution forms, and this is evaporated to dryness under reduced pressure. The potassium salt of the xanthine compound which remains is intensively dried under a high vacuum, 500 ml of dimethylformamide and 15.0 g (0.11 mol) of the tertiary alcohol from stage (a) are added and the mixture is stirred at 80° C. for 18 hours. The mixture is worked up analogously to Example 5b, whereupon 25.1 g of crude product (81.4% of theory) are obtained and can be purified by recrystallization from diisopropyl ether, with the addition of a little ethyl acetate, at the boiling point.

Yield: 19.2 g (62.3% of theory), melting point: 96°–98° C., $C_{15}H_{24}N_4O_3$ (molecular weight=308.4).

Analysis: Calculated: C 58.42% H 7.84% N 18.17%. Found: C 58.49% H 7.82% N 18.19%.

Other equivalent preparation procedures for this compound were methyl-branching of the oxoalkyl side chain of 3-methyl-1-(4-oxopentyl)-7-propylxanthine with methyllithium or a methylmagnesium halide analogously to Example 9, alkylation of 1-(4-hydroxy-4-methylpentyl)-3-methylxanthine with 1-bromo- or 1-chloropropane in the 7-position analogously to Example 3, and acid-catalyzed addition of water onto the olefinic double bond of 3-methyl-1-(4-methyl-3-pentenyl)-7-propylxanthine in accordance with Example 14 below.

EXAMPLE 13

3-Ethyl-1-(6-hydroxy-6-methylheptyl)-7-methylxan-
thine (a)

1-Bromo-6-hydroxy-6-methylheptane 89.8 g (1.2 mol) of methylmagnesium chloride in the form of a 20% strength solution in tetrahydrofuran are taken together with 500 ml of anhydrous ether, and a solution of 102.3 g (0.46 mol) of ethyl 6-bromohexanoate in 100 ml of dry ether is added dropwise at 0° to 5° C., while stirring. Thereafter, the mixture is subsequently stirred at room temperature for 30 minutes and while boiling under reflux for 2 hours, it is poured onto ice and 50% strength aqueous ammonium chloride solution is added until the precipitate formed has redissolved completely. The mixture is extracted several times with ether, the ethereal extract is washed in succession with aqueous sodium bisulfite and sodium bicarbonate solution and water, dried over sodium sulfate and filtered and the solvent is removed in vacuo. The residue is subjected to fractional distillation.

Yield: 80.2 g (83.4% of theory), boiling point (2 mbar) 77°–79° C., $C_8H_{17}OBr$ (molecular weight=209.1).

(b)

3-Ethyl-1-(6-hydroxy-6-methylheptyl)-7-methylxan-
thine

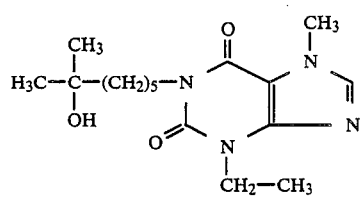

500 ml of dimethylformamide and 23.0 g (0.11 mol) of the tertiary bromo-alcohol from stage (a) are added to 23.2 g (0.1 mol) of 3-ethyl-7-methylxanthine potassium salt (prepared analogously to Example 12b) and the mixture is heated at 120° C. for 8 hours, while stirring. It is then worked up in accordance with Example 5b, whereupon an oily product is obtained which crystallizes completely after standing for a prolonged period, the crystals being recrystallized from diisopropyl ether.

Yield: 23.7 g (73.5% of theory), melting point: 86°–87° C., $C_{16}H_{26}N_4O_3$ (molecular weight=322.4).

Analysis: Calculated: C 59.61% H 8.13% N 17.38%. Found: C 59.68% H 8.16% N 17.54%.

The same compound was also obtained by reacting 3-ethyl-7-methyl-1-(6-oxoheptyl)-xanthine with methylmagnesium chloride or bromide analogously to Example 9, methylating 3-ethyl-1-(6-hydroxy-6-methylheptyl)-xanthine with methyl bromide, methyl iodide, a methyl sulfonate or dimethyl sulfate according to Example 3, and adding water onto the olefinic double bond of 3-ethyl-7-methyl-1(6-methyl-5-heptenyl)-xanthine in accordance with the following Example 14.

EXAMPLE 14

1-(5-Hydroxy-5-methylhexyl)-3,7-dimethylxanthine (a)

3,7-Dimethyl-1-(5-methyl-4-hexenyl)-xanthine

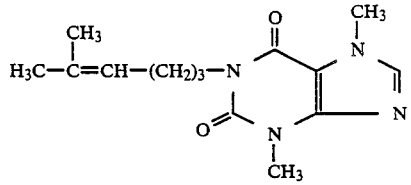

9.0 g (0.05 mol) of 3,7-dimethylxanthine, 8.0 g (0.06 mol) of 1-chloro-5-methyl-4-hexene and 8.3 g (0.06 mol) of potassium carbonate are stirred in 200 ml of dimethylformamide at 110° C. for 22 hours. After the solvent has been removed in vacuo, 100 ml of 1N sodium hydroxide solution are added and the mixture is extracted thoroughly with methylene chloride. The extract is extracted again by shaking with dilute sodium hydroxide solution, washed with water until neutral, dried and evaporated under reduced pressure and the residue is recrystallized from diisopropyl ether.

Yield: 10.1 g (73.1% of theory), melting point: 73°–75° C., $C_{14}H_{20}N_4O_2$ (molecular weight=276.3).

Analysis: Calculated: C 60.85% H 7.30% N 20.27%. Found: C 60.60% H 7.24% N 20.32%.

(b)

1-(5-Hydroxy-5-methylhexyl)-3,7-dimethylxanthine

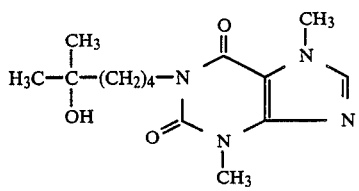

A solution of 9.5 g (0.034 mol) of the xanthine from stage (a) in 50 ml of dioxane and 50 ml of 50% strength sulfuric acid is stirred at 10° C. for 24 hours. Thereafter, the reaction mixture is rendered alkaline with 2N sodium hydroxide solution, while cooling with ice, and the product is extracted thoroughly with methylene chloride. The extract is washed in succession with 1N sodium hydroxide solution and water, dried and evaporated under reduced pressure. The residue can be purified by recrystallization from a mixture of diisopropyl ether and isopropanol.

Yield: 7.8 g (77.9% of theory), melting point: 120°–121° C., $C_{14}H_{22}N_4O_3$ (molecular weight=294.4).

Analysis: Calculated: C 57.13% H 7.53% N 19.03%. Found: C 57.21% H 7.74% N 18.78%.

Alternatively, it was possible, inter alia, to prepare the compound from 3,7-dimethylxanthine and 1-chloro-5-hydroxy-5-methylhexane analogously to Example 2 or 4, from 3,7-dimethyl-1-(5-oxohexyl)-xanthine and methylmagnesium chloride or bromide analogously to Example 9, and from the compound of Example 6 and a methylating agent analogously to Example 3.

EXAMPLE 55

7-(3,4-Dihydroxybutyl)-1-(5-hydroxy-5-methylhexyl)-3-methylxanthine (a)

7-(3-Butenyl)-3-methylxanthine

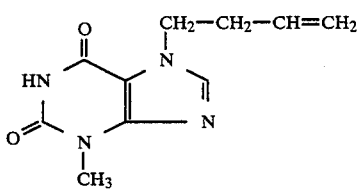

47 g (0.25 mol) of the monosodium salt of 3-methylxanthine (prepared as described in Example 1b) and 34.8 g (0.25 mol) of 97% strength 1-bromo-3-butene in 750 ml of dimethylformamide are stirred for 8 hours at 110° C. Thereafter, the precipitated sodium bromide is removed by filtration of the still hot reaction mixture, the filtrate is concentrated in vacuo, the solid residue is dissolved in 250 ml of 2N sodium hydroxide solution, the solution is heated to about 65° C. and 2N hydrochloric acid is added, while stirring, until the pH reaches 9. After cooling, the solid formed is filtered off under suction, washed salt-free with water, rinsed with methanol and then dried in vacuo.

Yield: 32 g (58.1% of theory), melting point: 242°–245° C., $C_{10}H_{12}N_4O_2$ (molecular weight=220.2).

(b)

7-(3-Butenyl)-1-(5-hydroxy-5-methylhexyl)-3-methylxanthine

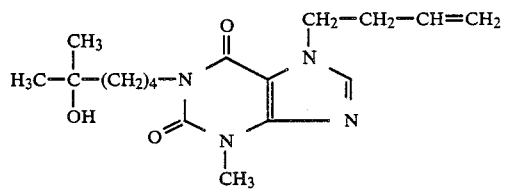

22 g (0.1 mol) of the xanthine from stage (a) are reacted with 16.6 g (0.11 mol) of 1-chloro-5-hydroxy-5-methylhexane (Example 1a) and 15.2 g (0.11 mol) of potassium carbonate in 500 ml of dimethylformamide under the experimental conditions described in Example 2, and the mixture is worked up. The reaction product is obtained in pure form without prior column chromatography, by recrystallization once from ethyl acetate with the addition of petroleum ether, at the boil.

Yield: 25.7 g (76.9% of theory), melting point: 105°–107° C., $C_{17}H_{26}N_4O_3$ (molecular weight=334.4).

(c)

7-(3,4-Epoxybutyl)-1-(5-hydroxy-5-methylhexyl)-3-methylxanthine

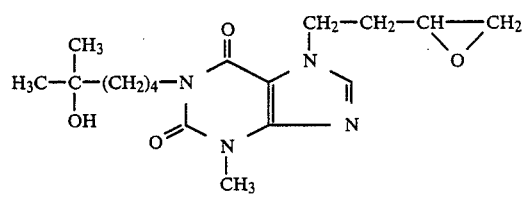

15.8 g (0.078 mol) of 85% strength 3-chloroperbenzoic acid are introduced, in the course of about 15 minutes at room temperature, into a solution of 22 g (0.066 mol) of the xanthine from stage (b) in 250 ml of chloroform under a nitrogen atmosphere and while stirring. After the mixture has been stirred for 48 hours at room temperature, it is washed in succession with 10% strength sodium dithionite solution, 10% strength sodium bicarbonate solution and water, dried and concentrated in vacuo, the epoxide being obtained in virtually quantitative yield as an oily product ($C_{17}H_{26}N_4O_4$; molecular weight=350.4), which can be used directly in the subsequent reaction stage (d).

(d)

7-(3,4-Dihydroxybutyl)-1-(5-hydroxy-5-methylhexyl)-3-methylxanthine

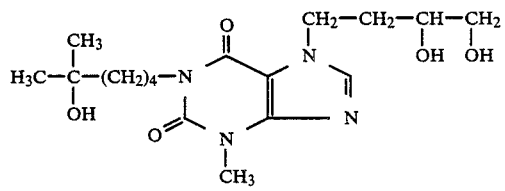

0.4 ml of perchloric acid (70% strength) is added to a solution of 23 g (0.065 mol) of the compound from stage (c) in a mixture of 120 ml of tetrahydrofuran and 80 ml of water, while stirring at room temperature. After stirring has been carried out for 5 days at room temperature, the reaction mixture is neutralized with saturated sodium bicarbonate solution and concentrated in vacuo, the residue is taken up in chloroform and the solution is purified by column chromatography over silica gel using a mixture of chlorform/methanol (volume ratio 10:1) as the mobile phase.

Yield: 19.4 g (81% of theory), melting point: 116°-118° C., $C_{17}H_{28}N_4O_5$ (molecular weight=368.4).

Analysis: Calculated: C 55.42% H 7.66% N 15.21%. Found: C 55.13% H 7.84% N 14.98%.

EXAMPLE 56

7-(2,3-Dihydroxypropyl)-1-(5-hydroxy-5-methylhexyl)-3-methylxanthine (a)

7-(2,3-Dihydroxypropyl)-3-methylxanthine

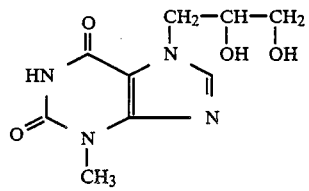

83 g (0.5 mol) of 3-methylxanthine are dissolved in 1250 ml of dimethylformamide, and 12 g (0.5 mol) of sodium hydride are added in portions at room temperature, while stirring. Stirring is continued for 30 minutes, after which 55.3 g (0.5 mol) of 1-chloro-2,3-propanediol in 100 ml of dimethylformamide are added dropwise and the mixture is heated for 18 hours at 110° C., while stirring. Working up is carried out as described in Example 55a).

Yield: 66.6 g (55.5% of theory), melting point: 302°-304° C., $C_9H_{12}N_4O_4$ (molecular weight=240.2).

(b)

7-(2,3-Dihydroxypropyl)-1-(5-hydroxy-5-methylhexyl)-3-methylxanthine

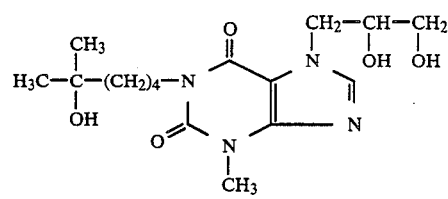

A mixture of 18 g (0.075 mol) of the xanthine compound from stage (a), 12.5 g (0.083mol) of 1-chloro-5-hydroxy-5-methylhexane (Example 1a) and 11.5 g (0.083 mol) of potassium carbonate in 500 ml of dimethylformamide is stirred for 18 hours at 110° C., after which the hot mixture is filtered and the filtrate is concentrated in vacuo. The oily crude product, which gradually crystallizes through, can advantageously be purified by filtration over a silica gel column using a chloroform/methanol (10:1) solvent mixture, followed by a final recrystallization from ethyl acetate with the addition of petroleum ether, at the boil.

Yield: 15.2 g (57.2% of theory), melting point: 105°-107° C., $C_{16}H_{26}N_4O_5$ (molecular weight=354.4).

Analysis: Calculated: C 54.22% H 7.39% N 15.81%. Found: C 53.87% H 7.47% N 15.71%.

TABLE 1

| | Compound according to formula I | | | |
|---|---|---|---|---|
| Example | $R^1$ | $R^2$ | $R^3$ | Melting point °C. |
| 1 | —H | —CH$_3$ | —(CH$_2$)$_4$—C(CH$_3$)(OH)—CH$_3$ | 228-230 |
| 2 | H$_3$C—C(CH$_3$)(OH)—(CH$_2$)$_4$— | —CH$_3$ | —(CH$_2$)$_4$—C(CH$_3$)(OH)—CH$_3$ | 93-95 |
| 3 | —C$_3$H$_7$ | —CH$_3$ | —(CH$_2$)$_4$—C(CH$_3$)(OH)—CH$_3$ | 59-60 |
| 4 | —CH$_3$ | —CH$_3$ | —(CH$_2$)$_4$—C(CH$_3$)(OH)—CH$_3$ | 106-107 |
| 5 | H$_3$C—C(CH$_3$)(OH)—(CH$_2$)$_4$— | —CH$_3$ | —CH$_2$—O—C$_2$H$_5$ | 102-103 |
| 6 | H$_3$C—C(CH$_3$)(OH)—(CH$_2$)$_4$— | —CH$_3$ | —H | 192-193 |

TABLE 1-continued

| Example | R¹ | R² | R³ | Melting point °C. |
|---|---|---|---|---|
| 7 | H$_3$C—C(CH$_3$)(OH)—(CH$_2$)$_4$— | —CH$_3$ | —CH$_2$—C(=O)—CH$_3$ | 78–80 |
| 8 | H$_3$C—C(CH$_3$)(OH)—(CH$_2$)$_4$— | —CH$_3$ | —CH$_2$—CH(OH)—CH$_3$ | 119–120 |
| 9 | H$_3$C—C(CH$_3$)(OH)—(CH$_2$)$_4$— | —CH$_3$ | —C$_3$H$_7$ | 81–82 |
| 10 | H$_3$C—CH$_2$—C(CH$_3$)(OH)—(CH$_2$)$_4$— | —CH$_3$ | —CH$_3$ | 83–84 |
| 11 | H$_3$C—C(CH$_3$)(OH)—(CH$_2$)$_4$— | —CH$_3$ | —CH$_2$—C(CH$_3$)(OH)—CH$_3$ | 121–123 |
| 12 | H$_3$C—C(CH$_3$)(OH)—(CH$_2$)$_3$— | —CH$_3$ | —C$_3$H$_7$ | 96–98 |
| 13 | H$_3$C—C(CH$_3$)(OH)—(CH$_2$)$_5$— | —C$_2$H$_5$ | —CH$_3$ | 86–87 |
| 14 | H$_3$C—C(CH$_3$)(OH)—(CH$_2$)$_4$— | —CH$_3$ | —CH$_3$ | 120–121 |
| 15 | H$_3$C—C(CH$_3$)(OH)—(CH$_2$)$_5$— | —CH$_3$ | —CH$_3$ | 112–113 |
| 16 | H$_3$C—C(CH$_3$)(OH)—(CH$_2$)$_5$— | —CH$_3$ | —C$_3$H$_7$ | 92–94 |
| 17 | H$_3$C—C(CH$_3$)(OH)—(CH$_2$)$_4$— | —C$_2$H$_5$ | —CH$_3$ | 98 |
| 18 | H$_3$C—C(CH$_3$)(OH)—(CH$_2$)$_4$— | —C$_2$H$_5$ | —C$_3$H$_7$ | 69–71 |
| 19 | H$_3$C—CH$_2$—C(CH$_3$)(OH)—(CH$_2$)$_4$— | —CH$_3$ | —C$_3$H$_7$ | 86–87 |
| 20 | H$_3$C—C(CH$_3$)(OH)—(CH$_2$)$_3$— | —CH$_3$ | —CH$_3$ | 117–118 |

TABLE 1-continued

| Example | R¹ | R² | R³ | Melting point °C |
|---|---|---|---|---|
| 21 | $H_3C-\underset{\underset{OH}{|}}{\overset{\overset{CH_3}{|}}{C}}-(CH_2)_3-$ | $-C_2H_5$ | $-CH_3$ | 94-95 |
| 22 | $H_3C-\underset{\underset{OH}{|}}{\overset{\overset{CH_3}{|}}{C}}-(CH_2)_3-$ | $-C_2H_5$ | $-C_3H_7$ | 92-93 |
| 23 | $H_3C-\underset{\underset{OH}{|}}{\overset{\overset{CH_3}{|}}{C}}-(CH_2)_2-$ | $-CH_3$ | $-CH_3$ | 146-147 |
| 24 | $H_3C-\underset{\underset{OH}{|}}{\overset{\overset{CH_3}{|}}{C}}-(CH_2)_2-$ | $-C_2H_5$ | $-CH_3$ | 122 |
| 25 | $H_3C-\underset{\underset{OH}{|}}{\overset{\overset{CH_3}{|}}{C}}-(CH_2)_2-$ | $-CH_3$ | $-C_3H_7$ | 135-137 |
| 26 | $-C_4H_9$ | $-C_4H_9$ | $-(CH_2)_2-\underset{\underset{OH}{|}}{\overset{\overset{CH_3}{|}}{C}}-CH_3$ | 69-70 |
| 27 | $H_3C-\underset{\underset{OH}{|}}{\overset{\overset{CH_3}{|}}{C}}-(CH_2)_5-$ | $-CH_3$ | $-CH_2-O-CH_3$ | 52-54 |
| 28 | $H_3C-\underset{\underset{OH}{|}}{\overset{\overset{CH_3}{|}}{C}}-(CH_2)_4-$ | $-CH_3$ | $-CH_2-O-CH_3$ | 92-94 |
| 29 | $H_3C-\underset{\underset{OH}{|}}{\overset{\overset{CH_3}{|}}{C}}-(CH_2)_4-$ | $-C_2H_5$ | $-CH_2-O-CH_3$ | 61-63 |
| 30 | $H_3C-\underset{\underset{OH}{|}}{\overset{\overset{CH_3}{|}}{C}}-(CH_2)_3-$ | $-CH_3$ | $-CH_2-O-CH_3$ | 99-101 |
| 31 | $H_3C-\underset{\underset{OH}{|}}{\overset{\overset{CH_3}{|}}{C}}-(CH_2)_3-$ | $-C_2H_5$ | $-CH_2-O-CH_3$ | 94-96 |
| 32 | $H_3C-\underset{\underset{OH}{|}}{\overset{\overset{CH_3}{|}}{C}}-(CH_2)_2-$ | $-CH_3$ | $-CH_2-O-CH_3$ | 105-107 |
| 33 | $H_3C-\underset{\underset{OH}{|}}{\overset{\overset{CH_3}{|}}{C}}-(CH_2)_4-$ | $-C_2H_5$ | $-CH_2-O-C_2H_5$ | 68-70 |
| 34 | $H_3C-\underset{\underset{OH}{|}}{\overset{\overset{CH_3}{|}}{C}}-(CH_2)_4-$ | $-CH_3$ | $-CH_2-O-C_3H_7$ | 83-85 |

TABLE 1-continued

Compound according to formula I

| Example | R¹ | R² | R³ | Melting point °C. |
|---|---|---|---|---|
| 35 | H₃C—O—(CH₂)₂— | —CH₃ | —(CH₂)₄—C(CH₃)(OH)—CH₃ | 63-65 |
| 36 | H₃C—C(CH₃)(OH)—(CH₂)₄— | —CH₃ | —(CH₂)₂—O—CH₃ | 98-99 |
| 37 | H₃C—C(CH₃)(OH)—(CH₂)₄— | —C₂H₅ | —(CH₂)₂—O—CH₃ | 71 |
| 38 | H₅C₂—O—(CH₂)₂— | —CH₃ | —(CH₂)₄—C(CH₃)(OH)—CH₃ | 77-79 |
| 39 | H₃C—C(CH₃)(OH)—(CH₂)₄— | —CH₃ | —(CH₂)₂—O—C₂H₅ | 75 |
| 40 | H₃C—C(CH₃)(OH)—(CH₂)₄— | —C₂H₅ | —(CH₂)₂—O—C₂H₅ | 52-54 |
| 41 | H₃C—O—(CH₂)₃— | —CH₃ | —(CH₂)₄—C(CH₃)(OH)—CH₃ | 45-47 |
| 42 | H₃C—C(CH₃)(OH)—(CH₂)₄— | —CH₃ | —(CH₂)₃—O—CH₃ | 83-84 |
| 43 | H₃C—C(CH₃)(OH)—(CH₂)₄— | —C₂H₅ | —(CH₂)₃—O—CH₃ | 72-73 |
| 44 | H₃C—C(CH₃)(OH)—(CH₂)₄— | —CH₃ | —CH₂—O—(CH₂)₂—O—CH₃ | 88-89 |
| 45 | H₃C—C(CH₃)(OH)—(CH₂)₄— | —C₂H₅ | —CH₂—O—(CH₂)₂—O—CH₃ | Oil |
| 46 | H₃C—C(CH₃)(OH)—(CH₂)₂— | —C₄H₉ | —CH₂—O—(CH₂)₂—O—CH₃ | 97-98 |
| 47 | H₃C—C(CH₃)(OH)—(CH₂)₄— | —CH₃ | —(CH₂)₂—O—(CH₂)₂—OC₂H₅ | 01 |
| 48 | H₃C—C(CH₃)(OH)—(CH₂)₄— | —C₂H₅ | —(CH₂)₂—O—(CH₂)₂—OC₂H₅ | Oil |

TABLE 1-continued

| | Compound according to formula I | | | |
|---|---|---|---|---|
| Example | R¹ | R² | R³ | Melting point °C. |
| 49 | H₃C—C(CH₃)(OH)—CH₂— | —CH₃ | —(CH₂)₄—C(CH₃)(OH)—CH₃ | 65–67 |
| 50 | H₃C—C(CH₃)(OH)—(CH₂)₄— | —CH₃ | —CH₂—CH₂—CH₂—OH | 78–80 |
| 51 | H₃C—C(CH₃)(OH)—(CH₂)₄— | —CH₃ | —(CH₂)₄—C(=O)—CH₃ | Oil |
| 52 | H₃C—C(CH₃)(OH)—(CH₂)₄— | —CH₃ | —(CH₂)₄—CH(OH)—CH₃ | 69–71 |
| 53 | H₃C—C(=O)—(CH₂)₄— | —CH₃ | —(CH₂)₄—C(CH₃)(OH)—CH₃ | Oil |
| 54 | H₃C—CH(OH)—(CH₂)₄— | —CH₃ | —(CH₂)₄—C(CH₃)(OH)—CH₃ | Oil |
| 55 | H₃C—C(CH₃)(OH)—(CH₂)₄— | —CH₃ | —(CH₂)₂—CH(OH)—CH₂(OH) | 116–118 |
| 56 | H₃C—C(CH₃)(OH)—(CH₂)₄— | —CH₃ | —CH₂—CH(OH)—CH₂(OH) | 105–107 |

PHARMACOLOGICAL TESTING AND RESULTS

1. Action on disturbed peripheral arterial circulation

In the last decade, the ideas about the pathophysiology and hence also the medicamentous therapy of chronic peripheral arterial occlusive diseases have undergone a considerable change inasmuch as the scientific and therapeutic interest has increasingly shifted from the macrocirculation to the microcirculation, and here in particular to the capillary vascular system, via which nutrition of the adjacent tissue takes place by diffusion-mediated substrate exchange. Disturbances in the microcirculation accordingly manifest themselves in cellular deficiency with resulting tissue ischemia, so that specific therapy must be directed towards eliminating the pathological inhomogeneity of the capillary nutritive circulation and thus normalizing the local partial pressure of oxygen ($pO_2$) in the ischemic tissues.

Testing of the compounds according to the invention for their action of improving supply to the tissue was therefore carried out with the aid of $pO_2$ measurements in the ischemic skeletal muscle using the experimental design described by D. W. Löbbers (Prog. Resp. Res. 3 (Karger, Basel 1969), pages 136–146) and M. Kessler (Prog. Resp. Res. 3 (Karger, Basel 1969), pages 147–152 and Anesthesiology 45 (1976), page 184), the standard therapeutic agent pentoxifylline also being included in the investigations as a comparison product.

The experimental animals used were male beagle dogs under sodium pentobarbital anesthesia (35 mg/kg intraperitoneally), on whose right hind extremity the femoral artery and a certain area of the lower leg muscle was exposed and on whose left hind extremity the femoral vein was exposed and a cannula inserted for infusion of the product and the femoral artery was exposed and a cannula inserted for blood pressure measurements. The animals were relaxed by administration of alcuronium chloride (0.1 mg/kg intravenously and then 0.05 mg/kg intraperitoneally every 30 minutes) and artificially ventilated in order on the one hand to avoid spontaneous contractions of the muscle with an adverse effect on the $pO_2$ measurements and on the other hand to guarantee a uniform supply of respiratory oxygen. Another catheter inserted into the femoral vein of the right hind extremity was used to monitor the lactate concentration in the venous outflow. A multiwire surface electrode (Eschweiler, Kiel) was now applied to the exposed area of muscle for continuous recording of the $pO_2$. As soon as the $pO_2$ curve had stabilized, the femoral artery was occluded with the aid of a clamp, after which the $pO_2$ in the muscle supplied by this vessel dropped rapidly, and then rose again slightly as a result of spontaneous opening of collateral vessels, and finally settled down at a greatly reduced level in comparison with the healthy muscle. At this point in time, the test substance, in aqueous solution, was either infused intravenously (i.v.) (0.6 mg/kg/minute) or administered intraduodenally (i.d.) in a dose of 25 mg/kg, and the rise in the $pO_2$ in the ischemic muscle was monitored by measurement. Venous blood was sampled in each case before and after occlusion and after administration of the substance, in order to determine the lactate washed out and hence to check the physiological status of the animals. The gas concentrations ($pO_2$ and $pCO_2$) and the pH in the arterial blood of the ischemic extremity were additionally checked at the start and at the end of each experiment.

In each experiment, the maximum percentage rise in the $pO_2$ following administration of the substance during vascular occlusion was used as the measurement parameter for the action of the product (n=2–11). A dimensionless activity index W was calculated from three measurement values for each compound by obtaining the product of the percentage frequency of positive experiments and the average percentage increase in $pO_2$ resulting from the positive individual values, this index both taking into account interindividual differences in the topology of the vascularization of the muscle and also recording responders and nonresponders to the test compounds and accordingly permitting a more reliable activity comparison amongst the individual products.

2. Action on regional cerebral circulation

The action of the compounds according to the invention on regional cerebral circulation was investigated with the aid of the heat conducting technique of F. A. Gibbs (Proc. Soc. exp. Biol. (N.Y.) 31 (1933), page 141 et seq.), H. Hensel (Naturwissenschaften 43 (1956), page 477 et seq.) and E. Betz (Acta Neurol. Scand. Suppl. 14 (1965), pages 29–37) on cats of both sexes under sodium pentobarbital anesthesia (35 mg/kg intraperitoneally), the standard therapeutic agent pentoxifylline again being used for comparison purposes. in this method, using a heat conduction probe attached to the surface of the brain in the region of the gyrus frontalis superior, the transport of heat from a heating point to an adjacent temperature measurement point in the probe, the transport of heat being directly proportional to the level of cerebral circulation, is determined. The percentage increase in the heat transport number λ after administration of the product is thus a measure of the improvement in circulation.

The compounds were administered intravenously in aqueous solution. The dose was 3 mg of test substance per kg of body weight. 3 to 5 individual experiments were carried out for each test product, and the average percentage increase in cerebral circulation was determined from the measurement data obtained.

3. Acute toxicity

The $LD_{50}$ ranges were determined by the standard method via the mortality which arose within 7 days in NMRI mice following a single intravenous (i.v.) or intraperitoneal (i.p.) dose (NMRI=Naval Medical Research Institute).

The results of these investigations, which clearly show the superiority of the compounds of formula I according to the invention over the standard product pentoxifylline, are summarized in the following Tables 2 and 3.

TABLE 2

Action on disturbed peripheral arterial circulation in the occlusion model on dogs and acute toxicity in mice

| Compound from Example | Mode of administration i.v.: 0.6 mg/kg/min i.d: 25 mg/kg | Activity index W (See Text) | Toxicity $LD_{50}$ (mouse) in mg/kg |
|---|---|---|---|
| 3 | i.v. | 1650 | i.v.: 100–200 |
|  | i.d. | 1250 |  |
| 4 | i.v. | 1300 | i.v.: 100–200 |
| 5 | i.v. (0.3 mg/kg/min) | 2080 | i.v.: 150–300 |
|  | i.d. | 2909 | i.p.: 300–600 |
| 6 | i.d. | 700 | i.v.: >200 |
| 8 | i.v. | 1400 | i.v.: <200 |
| 10 | i.d. | 1965 | i.v.: <200 |
| 12 | i.v. | 866 | i.v.: <200 |
|  | i.d. | 2337 |  |
| 14 | i.v. | 960 | i.v.: <200 |
| 16 | i.v. | 999 | i.p.: 150–300 |
| 17 | i.v. | 1525 | i.v.: <200 |
| 18 | i.v. | 1578 | i.v.: 100–200 |
| 28 | i.d. | 2100 | i.v.: <200 |
| 32 | i.v. | 2650 | i.v.: <200 |
|  | i.d. | 566 | i.v.: <200 |
| 37 | i.v. | 1400 | i.v.: <200 |
|  | i.d. | 950 |  |
| 39 | i.v. | 1567 | i.v.: <200 |
|  | i.d. | 1996 |  |
| 44 | i.v. | 1199 | i.v.: <200 |
| 50 | i.v. | 2631 | i.v.: <200 |
|  | i.d. | 733 |  |
| Pentoxifylline | i.v. | 891 | i.v.: 187–209 |
|  | i.d. | 643 | i.p.: 219–259 |

TABLE 3

Action on the regional cerebral circulation of anesthetized cats following an intravenous dose of 3 mg/kg and acute toxicity in mice

| Compound from Example | Average increase in cerebral circulation as $\overline{\Delta\lambda}$ in % | Toxicity $LD_{50}$ (mouse) in mg/kg |
|---|---|---|
| 3 | 15.5 | i.v.: 100–200 |
| 9 | 9.4 | i.v.: 100–200 |
| 16 | 25.8 | i.p.: 150–300 |
| 17 | 9.4 | i.v.: >200 |
| 18 | 9.4 | i.v.: 100–200 |
| 22 | 12.0 | i.v.: >200 |
| 27 | 10.3 | i.v. >200 |
| 43 | 19.8 | i.v.: >200 |
| 48 | 14.6 | i.v.: >200 |
| Pentoxifylline | 8.6 | i.v. 187–209 |
|  |  | i.p.: 219–259 |

The clear superiority of the compounds according to the invention, in particular compared with the xanthine derivative most frequently used for the therapy of disturbances in peripheral and cerebral circulation, pentoxifylline, was also confirmed impressively in other specific experiments.

It is today generally recognized that exclusively vasodilating drugs or agents with a very potent vasodilating action component are unsuitable for the treatment of disturbances in the microcirculation because, on the one hand, the physiological vasodilatory reserve as a rule is already completely exhausted, and on the other hand there is the risk of a steal phenomenon, which means a harmful redistribution of the nutritive blood flow in the microcirculation at the expense of the already undersupplied diseased tissue. The inhibiting effect on vascular contraction induced with norfenefrine on the isolated perfused rabbit ear was therefore investigated. Here, for example, the compound from Example 5 shows no inhibition of the norfenefrine action up to a concentration of 100 μg/ml, whilst pentoxifylline had a dose-dependent dilating effect on the norfenefrine-contracted vessels in the concentration range from 10 to 100 μg/ml.

In a chronic experiment on rats with unilateral occlusion of the iliac artery, it was possible to demonstrate that the compounds of the formula I are capable of having a favorable influence on the metabolism in the ischemic skeletal muscle. In particular, when the animals were treated, for example, with the compound from Example 5 for 5 weeks, in each case 3 mg/kg being administered intraperitoneally three times daily, it was possible to demonstrate with the aid of histochemical staining methods that the proportion of oxidative fibers in the two muscles investigated in the ischemic extremity (tibialis anterior and extensor digitorum longus) had increased significantly. In contrast, pentoxifylline had no direct influence on muscular metabolism in a similar experimental procedure.

The superiority of the xanthines of the formula I was also to be seen from another chronic experiment in which the influence on the contractility of the ischemic skeletal muscle in rats with a ligated right femoral artery was investigated. The animals received the particular test product in a daily oral dose of 25 mg/kg by a stomach tube for 20 days. Thereafter, the fatigability of the ischemic muscle on electrical stimulation with about 80 contractions per minute was determined via the decrease in contractile force after stimulation for 1, 15 and 45 minutes in comparison with untreated control animals. In this test, for example, the compound of Example 5—evidently as a result of optimization of metabolism—effected a significant improvement in muscular performance in the ischemic extremity, even normal contractility values like those in the left healthy (non-ischemic) muscle of untreated animals being reached. This improvement was accompanied by an increase in the mitochondrial respiratory control rate (RCR). Pentoxifylline proved to have no action in these experiments. The compounds according to the invention are accordingly also suitable for the treatment of muscular energy metabolism disorders of various causes, particularly mitochondrial myopathy.

The pharmaceutical products according to the invention are suitable for use in both human and veterinary medicine.

We claim:

1. Tertiary hydroxyalkyl xanthines of the general formula I

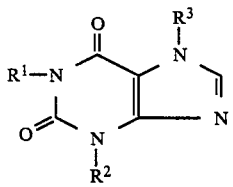

wherein at least one of the groups $R^1$ and $R^3$ is a tertiary hydroxyalkyl group of the formula

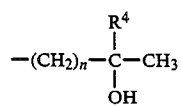

in which $R^4$ is an alkyl group having up to 3 carbon atoms and n is an integer in the range from 2 to 5, the other group, if any, of $R^1$ or $R^3$ is hydrogen or an aliphatic hydrocarbon radical $R^5$ having up to 6 carbon atoms, the carbon chain of which may be interrupted by up to 2 oxygen atoms or substituted with an oxo group or up to two hydroxy groups, $R^2$ is an alkyl group having 1 to 4 carbon atoms.

2. Compounds according to claim 1, wherein $R^2$ is methyl or ethyl.

3. Compounds according to claim 1 wherein only one of the two groups $R^1$ and $R^3$ represents the tertiary hydroxyalkyl group defined in claim 1.

4. Compounds according to claim 1 wherein a hydroxy or oxo group contained in the group $R^5$ is separated from the nitrogen atom by at least two carbon atoms.

5. Compounds according to claim 3, wherein in formula I $R^1$ or $R^3$ is [(ω-1)-hydroxy-(ω-1)-methyl]pentyl, -hexyl or -heptyl.

6. Compounds according to claim 3 wherein in formula I $R^1$ represents the tertiary hydroxyalkyl group.

7. Compounds according to claim 6 wherein $R^1$ is [(ω-1)-hydroxy-(ω-1)-methyl]-pentyl, -hexyl or -heptyl, $R^2$ is methyl or ethyl and $R^3$ is alkyl, hydroxyalkyl or alkoxyalkyl each having 1 to 4 carbon atoms.

8. A compound according to claim 7 which is 7-ethoxymethyl-1-(5-hydroxy-5-methylhexyl)-3-methylxanthine.

9. A pharmaceutical composition comprising an amount, effective for use as a pharmaceutical in the prophylaxis or therapy of peripheral or cerebral disturbed blood circulation or both, of at least one compound according to claim 7.

10. A pharmaceutical composition comprising an amount, effective for use as a pharmaceutical in the prophylaxis or therapy of peripheral or cerebral disturbed blood circulation or both, of at least one compound of the formula I according to claim 1.

11. A pharmaceutical composition according to claim 10 for use in the prophylaxis or treatment of the peripheral occlusive arterial disease.

12. A pharmaceutical composition comprising an amount, effective for use as a pharmaceutical in the treatment of disorders of the skeletal muscle energy metabolism, of at least one compound of the formula I according to claim 1.

13. A pharmaceutical composition according to claim 12 for use in the treatment of disorders of mitochondrial myopathies.

14. A method of treating a patient suffering from peripheral or cerebral disturbed blood circulation or both which comprises administering to said patient a pharmaceutical composition according to claim 10.

15. A method of treating a patient suffering from disorders of the skeletal muscle energy metabolism which comprises administering to said patient a pharmaceutical composition according to claim 12.

16. A method according to claim 14 for treating a patient suffering from peripheral occlusive arterial disease.

17. A method according to claim 15 for treating a patient suffering from disorders of mitochondrial myopathies.

18. A method of treating a patient suffering from peripheral or cerebral disturbed blood circulation or of disorders of the skeletal muscle energy metabolism which comprises administering to said patient an effective amount of at least one compound of the formula I according to claim 1.

19. A method according to claim 18 for treating a patient suffering from peripheral occlusive arterial disease.

20. A method according to claim 18 for treating a patient suffering from disorders of mitochondrical myopathies.

* * * * *